United States Patent [19]

Bloom et al.

[11] 4,359,574

[45] Nov. 16, 1982

[54] THIAZINE-1,1-DIOXIDE AND ISOTHIAZOLE-1,1-DIOXIDE DERIVATIVES

[75] Inventors: Stanley M. Bloom, Waban; Alan L. Borror, Lexington; James W. Foley, Andover, all of Mass.

[73] Assignee: Polaroid Corporation, Cambridge, Mass.

[21] Appl. No.: 175,291

[22] Filed: Aug. 4, 1980

Related U.S. Application Data

[62] Division of Ser. No. 836,010, Sep. 23, 1977, abandoned.

[51] Int. Cl.³ ............... C07D 275/04; C07D 279/08
[52] U.S. Cl. ................... 544/135; 544/58.7; 544/62; 544/368; 260/239 R; 546/209; 548/208; 548/209
[58] Field of Search ............... 548/209, 208; 260/243.3, 239 R; 546/209; 544/62, 58.7, 368, 135

[56] References Cited

U.S. PATENT DOCUMENTS

| | | | |
|---|---|---|---|
| 4,178,446 | 12/1979 | Bloom et al. | 548/209 |
| 4,178,447 | 12/1979 | Borror et al. | 548/209 |
| 4,191,689 | 3/1980 | Bloom et al. | 544/135 |
| 4,204,061 | 5/1980 | Bloom et al. | 544/368 |
| 4,255,578 | 3/1981 | Cincotta | 544/135 |
| 4,259,493 | 3/1981 | Foley | 544/135 |

FOREIGN PATENT DOCUMENTS 40-20779  5/1974  Japan.

OTHER PUBLICATIONS

Mustafa et al., J. Chem. Soc., (1952), pp. 1339–1340.
Abramovitch et al., J. Chem. Soc., Perkin Trans. I, (1974) (22), pp. 2589–2594.
Dutt, J. Chem. Soc. 121, pp. 2389–2394, (1922).
McClelland et al., J. Chem. Soc., pp. 323–327, (1940).
McOmie, Protecting Groups in Org. Chem., (1973), pp. 145, 146, 157, 158, 159.
Beilstein's, Handbuch der Organischen Chemie 27, p. 534, (1944).
Royals, Advanced Organic Chemistry, p. 617, (1962).
C.A. 91, 58712d, (1979), (Abstracting Ger. Offen. 2841 322).
C.A. 91, 58713e, (1979), (Abstracting Ger. Offen. 2841 321).

*Primary Examiner*—Nicholas S. Rizzo
*Attorney, Agent, or Firm*—Sybil A. Campbell

[57] ABSTRACT

In one aspect, this invention relates to a method of synthesizing certain 3-(4'-OH-carbocyclic aryl)-3-(carbocyclic aryl)-2,3-dihydrobenz[d]isothiazole-1,1-dioxides (and -2,3-dihydronaphtho[1,8-de]-1,2-thiazine-1,1-dioxides) by reacting a 3-(4'-OP-carbocyclic aryl)-3-(carbocyclic aryl)-2,3-dihydrobenz[d]isothiazole-1,1-dioxide (or a 3-(4'-OP-carbocyclic aryl)-3-(carbocyclic aryl)-2,3-dihydronaphtho[1,8-de]-1,2-thiazine-1,1-dioxide) wherein P is a protecting group with a carboxylic acid halide in pyridine to yield the corresponding 2-carbonyl derivative followed by removing the protecting group with weak acid to give the product. Optionally, the acylation step may be carried out by sequentially reacting the starting compound with an alkali metal hydride to give the corresponding 2-alkali metal salt and then reacting with the carboxylic acid halide in a suitable inert organic solvent. The products produced comprise phenol and 1-naphthol sulfam(na)phthaleins useful, for example, as photographic optical filter agents and filter agent precursors.

In another aspect, the present invention relates to the carbonyl-substituted and alkali metal-substituted 2,3-dihydrobenz[d]isothiazole-1,1-dioxides and 2,3-dihydronaphtho[1,8-de]-1,2-thiazine-1,1-dioxides produced as intermediates in the above synthesis.

47 Claims, No Drawings

THIAZINE-1,1-DIOXIDE AND ISOTHIAZOLE-1,1-DIOXIDE DERIVATIVES

This is a division of application Ser. No. 836,010, filed Sept. 23, 1977, now abandoned.

BACKGROUND OF THE INVENTION

1. Field of the Invention

This invention relates to a novel method of preparing certain phenol and 1-naphthol sulfamphthaleins and sulfamnaphthaleins useful as reagents in photography.

2. Description of the Prior Art

Various procedures have been reported for synthesizing 3-substituted-benz[d]isothiazole-1,1-dioxides and 3,3-disubstituted-2,3-dihydrobenz[d]isothiazole-1,1-dioxides from saccharin (3-oxo-2,3-dihydrobenz[d]isothiazole-1,1-dioxide) and from saccharin pseudo-chloride (3-chlorobenz[d]isothiazole-1,1-dioxide). As reported by A. Mustafa et al, *J. Chem Soc.*, 1952, p. 1339, the treatment of saccharin pseudo-chloride with excess phenylmagnesium bromide gave the corresponding 3,3-diphenyl-2,3-dihydrobenz[d]isothiazole-1,1-dioxide in almost quantitative yield. Methyl-, ethyl-, n-propyl- and n-butylmagnesium halides were reported by these authors to react analogously. R. A. Abramovitch et al, *J. Chem. Soc., Perkin Trans I,* 1974(22), p. 2589, reviewed and reinvestigated the reactions of saccharins with alkyl and aryl Grignard reagents and found that either the 3-alkyl (or 3-aryl)-benz[d]isothiazole-1,1-dioxide and/or the open-chain tertiary alcohol, o-$CR_2OH$ benzenesulfonamide wherein R is alkyl (or aryl) were obtained with one exception. When saccharin was treated with an excess of phenylmagnesium bromide in boiling tetrahydrofuran, 3,3-diphenyl-2,3-dihydrobenz[d]isothiazole-1,1-dioxide was obtained as the minor product together with the open-chain tertiary alcohol.

R. A. Abramovitch et al also investigated the reaction of saccharin and saccharin pseudo-chloride with organolithium compounds and found that the reaction of saccharin with alkyl- and aryllithium compounds, such as, n-butyllithium and p-methoxyphenyllithium in tetrahydrofuran at $-78°$ C. gave the corresponding 3-substituted-benz[d]isothiazole-1,1-dioxide exclusively. In addition to this general method for synthesizing 3-alkyl (or 3-aryl)-benz[d]isothiazole-1,1-dioxides, the authors reported that the reaction of the pseudo-chloride with organolithium compounds, such as, n-butyllithium in tetrahydrofuran at $-78°$ C. gave the corresponding 3,3-disubstituted-2,3-dihydrobenz[d]isothiazole-1,1-dioxide as the major product.

Besides the reactions with Grignard and organolithium reagents, Friedel-Crafts reactions with the saccharins also have been disclosed. Dutt, *J. Chem. Soc.*, 121, p. 2389 (1922) reported the condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure of 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali and also, that the compound corresponding to the structure given could not be synthesized by repeating the procedures reported by Dutt.

The present invention is concerned with a method of preparing sulfamphthaleins (3,3-disubstituted-2,3-dihydrobenz[d]isothiazole-1,1-dioxides) and sulfamnaphthaleins (3,3-disubstituted-2,3-dihydronaphtho[1,8-de]-1,2-thiazine-1,1-dioxides) derived from phenols and 1-naphthols which possess a carbonyl moiety in the 2-position, i.e., on the N atom of the sulfam(na)phthalein ring and with intermediates useful in the preparation thereof.

SUMMARY OF THE INVENTION

It is, therefore, the primary object of the present invention to provide a novel method of synthesizing certain N-substituted sulfam(na)phthaleins derived from phenols and 1-naphthols.

It is another object of the present invention to provide novel intermediates useful in the synthesis of said N-substituted sulfam(na)phthaleins.

It is a further object of the present invention to provide a method of synthesizing said intermediates.

Other objects of this invention will in part be obvious and will in part appear hereinafter.

This invention accordingly comprises the process involving the several steps and the relation and order of one or more of such steps with respect to each of the others and the product possessing the features, properties and the relation of elements which are exemplified in the following detailed disclosure and the scope of the application of which will be indicated in the claims.

According to the present invention, N-substituted sulfamphthaleins are synthesized (1) by reacting (a) a 3-(4'-OP-carbocyclic aryl)-3-(carbocyclic aryl)-2,3-dihydrobenz[d]isothiazole-1,1-dioxide wherein P is a protecting group with (b) a carboxylic acid halide in pyridine to yield (c) the corresponding 2-Z-3-(4'-OP-carbocyclic aryl)-3-(carbocyclic aryl)-2,3-dihydrobenz[d]isothiazole-1,1-dioxide wherein Z is a carbonyl moiety and (2) removing the protecting group to yield the corresponding 2-Z-3-(4'-OH-carbocyclic aryl)-3-(carbocyclic aryl)-2,3-dihydrobenz[d]isothiazole-1,1-dioxide. The sulfamnaphthaleins are synthesized in the same manner except that a 3-(4'-OP-carbocyclic aryl)-3-(carbocyclic aryl)-2,3-dihydronaphtho[1,8-de]-1,2-thiazine-1,1-dioxide is reacted with the acylating agent followed by deblocking of the —OH group to give the product. Optionally, the acylating step may be carried out by sequentially reacting said (a) with an alkali metal hydride to give the corresponding N-alkali metal salt which is then reacted with the acid halide to yield (c).

The subject method is generally applicable to the synthesis of certain N-substituted sulfam(na)phthaleins derived from phenols and 1-naphthols, namely, sulfam(na)phthaleins wherein one of the 3,3 substituents is a 4'-hydroxyphenyl moiety, unsubstituted or substituted with one or more groups compatible with organometallic reagents, or a 4'-hydroxynaphthyl moiety, unsubstituted or substituted with one or more groups compatible with organometallic reagents. The other of the 3,3 substituents may be the same, or it may be different as will be discussed below.

The subject intermediates comprise the compounds (c) wherein the N atom of the sulfam(na)phthalein ring is substituted with a carbonyl moiety and the N-alkali metal salts produced in the optional acylation step. In the subject intermediates, the functional hydroxy group of the 4'-hydroxyphenyl or 4'-hydroxynaphthyl moiety is blocked by a protecting group.

For a fuller understanding of the nature and objects of the present invention, reference should be had to the following detailed description.

DESCRIPTION OF THE PREFERRED EMBODIMENTS

Specifically, the method of the present invention for synthesizing N-substituted sulfam(na)phthaleins comprises (1) reacting (a) a compound of the formula

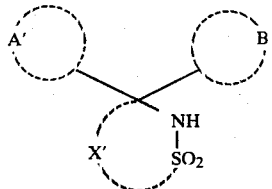

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety, unsubstituted or substituted with one or more substituents compatible with organometallic reagents, the same or different, or a naphthyl moiety unsubstituted or substituted with one or more substituents compatible with organometallic reagents, the same or different; P is a protecting group; and X' represents the atoms necessary to complete a 2,3-dihydrobenz[d]isothiazole-1,1-dioxide moiety or a 2,3-dihydronaphtho[1,8-de]-1,2-thiazine-1,1-dioxide moiety with (b) an acid halide of the formula W-Z wherein W is chloro or bromo and Z is a carbonyl moiety containing a

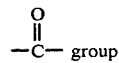

in pyridine at a temperature between about 0° C. and 100° C. to yield (c) the corresponding acylated compound having the formula

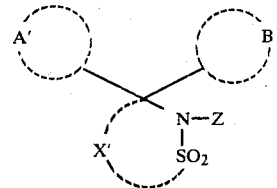

wherein A', B and X' have the same meaning given above and Z is said carbonyl moiety and said

is bonded to said N atom; and (2) treating the last-named compound with an organic or inorganic acid at a pH between about 0.1 and 5.0 to give (d) the product having the formula

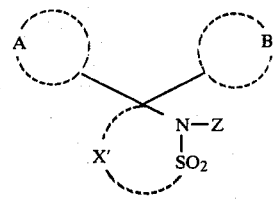

wherein A is a 4'-OH-1'-phenyl moiety, unsubstituted or substituted with one or more substituents compatible with organometallic reagents, the same or different, or a 4'-OH-1'-naphthyl moiety, unsubstituted or substituted with one or more substituents compatible with organometallic reagents, the same or different; and B, X' and Z have the same meaning given above.

As mentioned previously, step (1) optionally may be conducted by sequentially reacting compound (a) with MH wherein M is lithium, sodium or potassium in an inert organic solvent at a temperature between about 0° and 100° C. to give the corresponding N-alkali metal salt having the formula

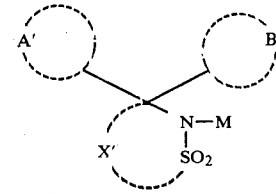

wherein A', B, X' and M have the same meaning given above followed by reacting said N-alkali metal salt with said carboxylic acid halide (b) to give said N-acylated compound (c).

The above reaction scheme is illustrated below using as specific reactants, 3-(3',5'-dimethyl-4'-methoxymethoxy-1'-phenyl)-3-(4''-N-morpholinyl-1''-phenyl)-2,3-dihydrobenz[d]isothiazole-1,1-dioxide, sodium hydride and 2-cyanoethylchloroformate.

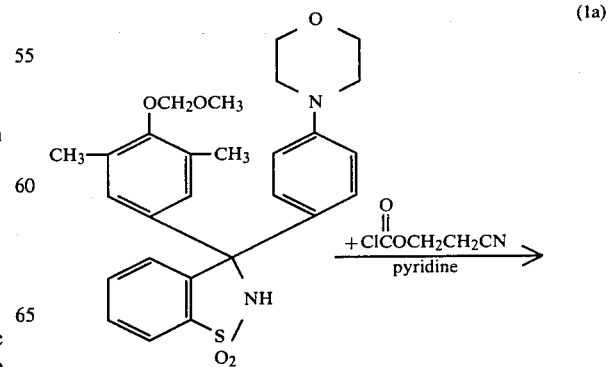

(1a)

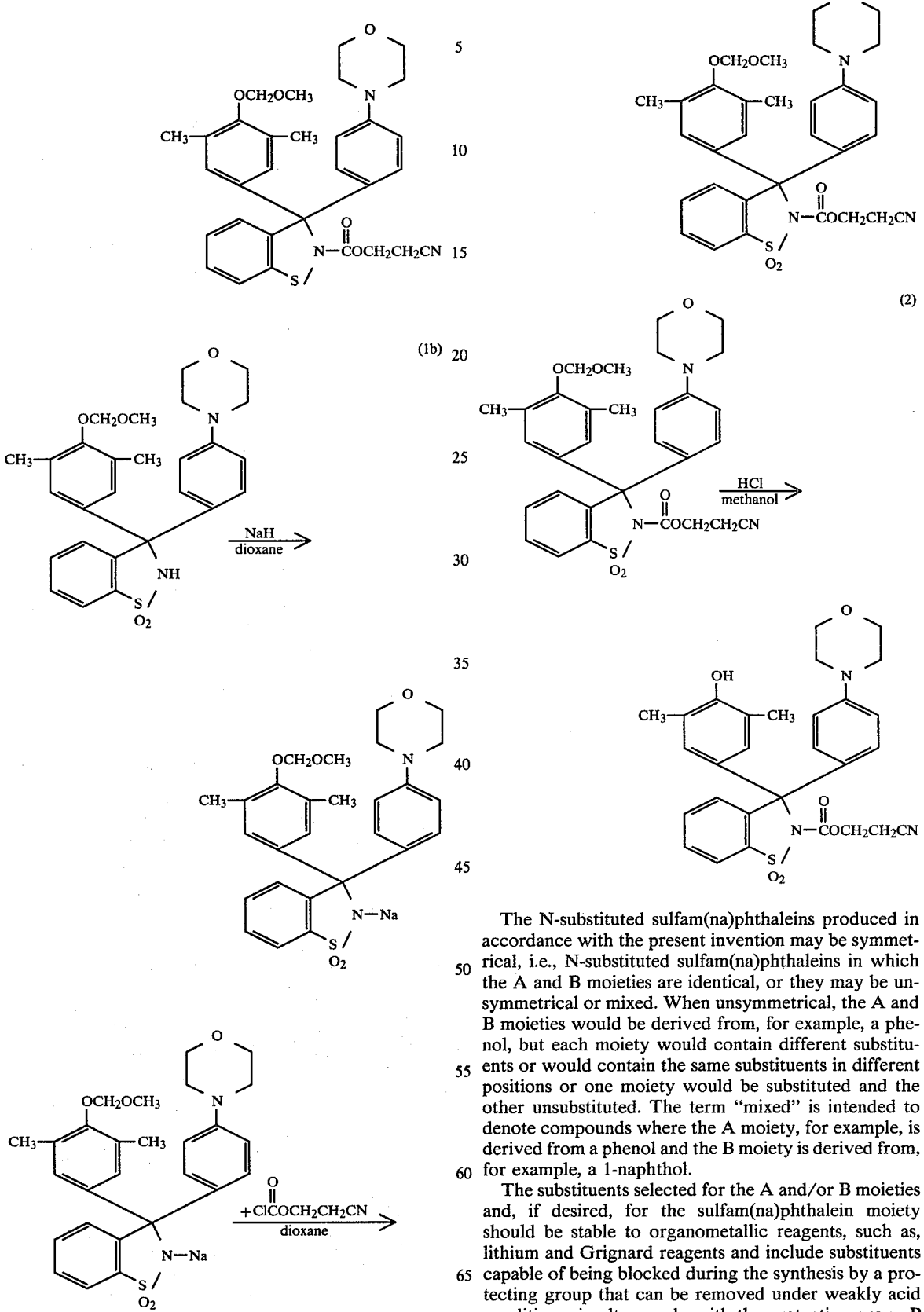

The N-substituted sulfam(na)phthaleins produced in accordance with the present invention may be symmetrical, i.e., N-substituted sulfam(na)phthaleins in which the A and B moieties are identical, or they may be unsymmetrical or mixed. When unsymmetrical, the A and B moieties would be derived from, for example, a phenol, but each moiety would contain different substituents or would contain the same substituents in different positions or one moiety would be substituted and the other unsubstituted. The term "mixed" is intended to denote compounds where the A moiety, for example, is derived from a phenol and the B moiety is derived from, for example, a 1-naphthol.

The substituents selected for the A and/or B moieties and, if desired, for the sulfam(na)phthalein moiety should be stable to organometallic reagents, such as, lithium and Grignard reagents and include substituents capable of being blocked during the synthesis by a protecting group that can be removed under weakly acid conditions simultaneously with the protecting group P in step (2) of the general synthesis described above.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

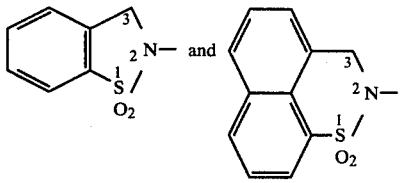

Typical of the sulfam(na)phthaleins that may be prepared according to the present invention are those represented by the following formula:

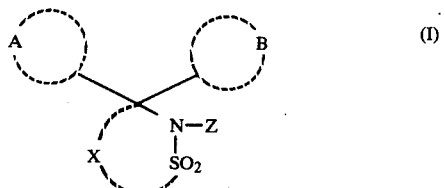

wherein A is a 4'-hydroxy-1'-phenyl moiety, unsubstituted or substituted with one or more substituents compatible with organometallic reagents, the same or different, or a 4'-hydroxy-1'-naphthyl moiety, unsubstituted or substituted with one or more substituents compatible with organometallic reagents, the same or different; B is a phenyl moiety, unsubstituted or substituted with one or more substituents compatible with organometallic reagents, the same or different, or a naphthyl moiety, unsubstituted or substituted with one or more substituents compatible with organometallic reagents, the same or different; X represents the carbon atoms necessary to complete a 2,3-dihydrobenz[d]isothiazole-1,1-dioxide moiety or a 2,3-dihydronaphtho[1,8-de]-1,2-thiazine-1,1-dioxide moiety; and Z represents a carbonyl moiety containing a

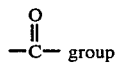 group bonded to said N atom.

Typical substituents compatible with or capable of being protected to be compatible with organometallic reagents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—NH—SO$_2$R$^o$ wherein R$^o$ is alkyl, aryl, alkaryl or aralkyl); sulfamoyl (—SO$_2$—N-H—R$^o$ wherein R$^o$ has the same meaning given above); acyl

wherein R$^o$ has the meaning given above); sulfonyl (—SO$_2$—R$^o$ wherein R$^o$ has the same meaning given above); sulfo; cyano, carboxy, hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine).

In a preferred embodiment of the present invention, the method of synthesizing N-substituted sulfam(na)phthaleins comprises (1a) reacting (a) a compound of the formula

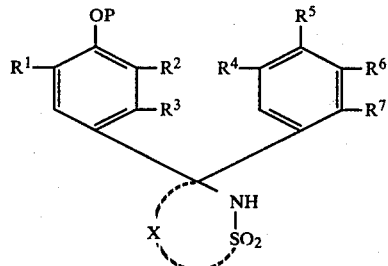

wherein P is a protecting group, R$^1$ and R$^2$ each are selected from hydrogen, alkyl, alkoxy, chloro and fluoro; R$^3$ is hydrogen, alkyl, alkoxy or —OP; R$^2$ and R$^3$ taken together represent the carbon atoms necessary to complete a fused benzene ring; R$^4$ and R$^6$ each are selected from hydrogen, alkyl, alkoxy, chloro and fluoro; R$^5$ is hydrogen, alkyl, alkoxy, —OP$^I$ wherein P$^I$ is a protecting group, —N,N-(dialkyl)-amino, —N,N-(w-R$^8$alkyl)$_2$amino wherein R$^8$ is halo or —OP$^{II}$ wherein P$^{II}$ is a protecting group, NHCOCH$_3$, piperidino, pyrrolidino, N-methylpiperazino, morpholino, thiomorpholino or tetrahydro-2H,4H-1,3,6-dioxazocino; R$^7$ is hydrogen, alkyl, alkoxy or —OP$^{III}$ wherein P$^{III}$ is a protecting group usually the same as P$^I$ or P$^{II}$; R$^6$ and R$^7$ taken together represent the carbon atoms necessary to complete a fused benzene ring; R$^4$, R$^5$ and R$^6$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and (b) an acid halide of the formula

wherein W is chloro or bromo and R$^9$ is methyl, methyl substituted with at least one halo group selected from chloro, bromo and fluoro, alkoxy having 1 to 4 carbon atoms, phenyl, phenyl substituted preferably in the para position with alkyl having 1 to 4 carbon atoms or —N,N-(dialkyl)amino, phenyl substituted with at least one electron-withdrawing group, phenoxy, phenoxy substituted with at least one electron-withdrawing group, —O(CH$_2$)$_2$Y wherein Y is an electron-withdrawing group and phenyl substituted in the ortho position with —CH$_2$R$^{10}$ wherein R$^{10}$ is chloro or bromo in pyridine at a temperature between about 0° and 100° C. to yield (c) the corresponding N-acylated compound of the formula

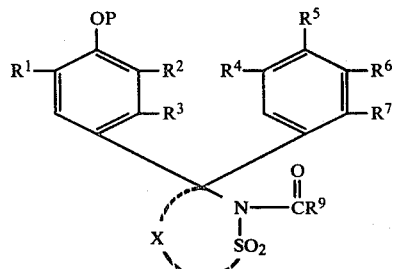

wherein P, R$^1$, R$^2$, R$^3$, R$^4$, R$^5$, R$^6$, R$^7$, R$^9$ and X have the same meaning given above; or (1b) sequentially reacting said compound (a) with MH wherein M is an alkali metal selected from lithium, sodium and potassium in an inert organic solvent at a temperature between about 0° and 100° C. to give the corresponding N-alkali metal salt having the formula

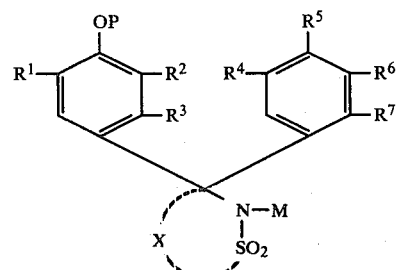

wherein P, R$^1$, R$^2$, R$^3$, R$^4$, R$^5$, R$^6$, R$^7$, X and M have the same meaning given above and then reacting said N-alkali metal salt with said acid halide (b) to give said N-acylated compound (c); and (2) treating said compound (c) between about 20° and 100° C. with an organic or inorganic acid at a pH between about 0.1 and 5 to yield the product having the formula

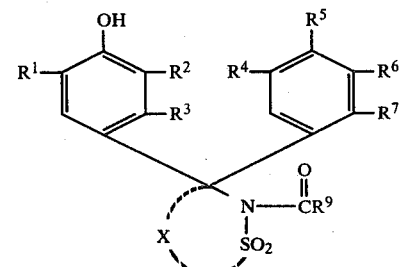

wherein R$^1$, R$^2$, R$^3$, R$^4$, R$^5$, R$^6$, R$^7$, R$^9$ and X have the same meaning given above except that said —OP of R$^3$, said —OP$^I$ and —OP$^{II}$ of R$^5$, and said —OP$^{III}$ of R$^7$ each are —OH. By electron-withdrawing group is intended "a group with a positive sigma value as defined by Hammett's Equation".

Usually, the alkyl and alkoxy substituents comprising R$^1$, R$^2$, R$^3$, R$^4$, R$^5$, R$^6$ and R$^7$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N-(dialkyl)amino and —N,N-(w-R$^8$alkyl)$_2$amino substituents usually are lower alkyl having 1 to 4 carbon atoms and R$^8$, when halo, is preferably chloro. Examples of electron-withdrawing groups include fluoro, chloro and bromo; nitro; cyano; —SO$_2$CH$_3$;

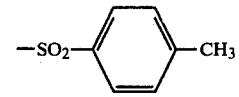

and —COCH$_3$. The value for these and other groups have been reported by Eugen Müller, Methoden Der Organischen Chemie, Georg Thieme Verlag, Stuttgart, 1970, p. 78.

In a particularly preferred embodiment, X represents the atoms necessary to complete 2,3-dihydrobenz[d]isothiazole-1,1-dioxide.

Specific examples of compounds that may be prepared according to the method of the present invention are as follows:

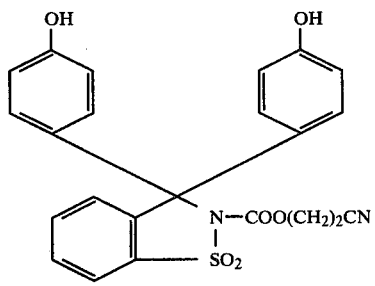
(1)

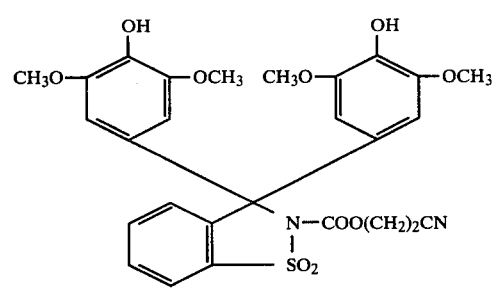
(2)

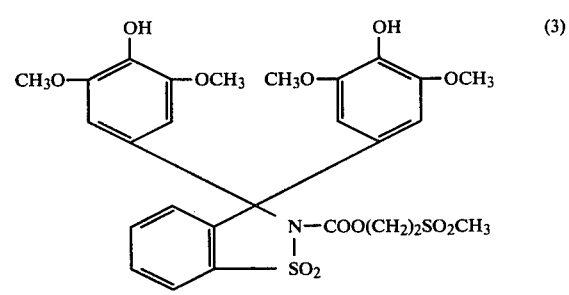
(3)

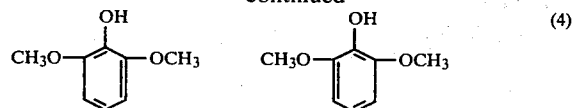 (4)
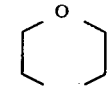 (10)
 (5)
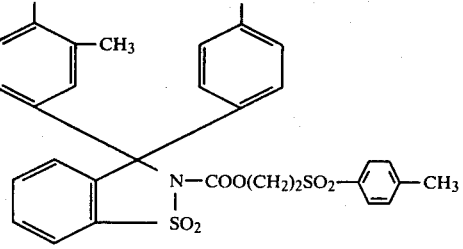
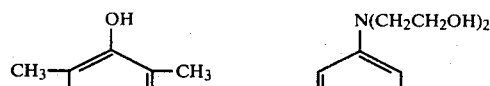 (6)
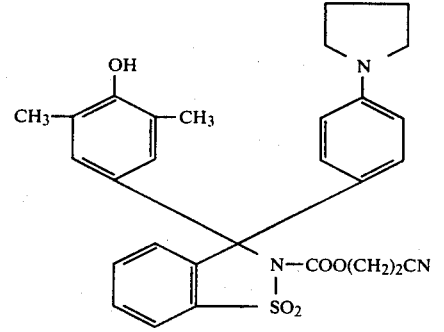 (11)
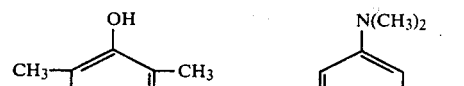 (7)
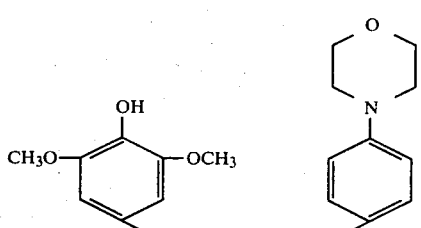
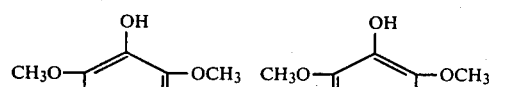 (8)
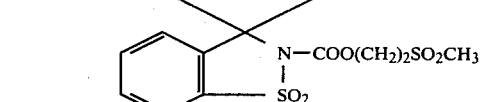 (12)
 (9)
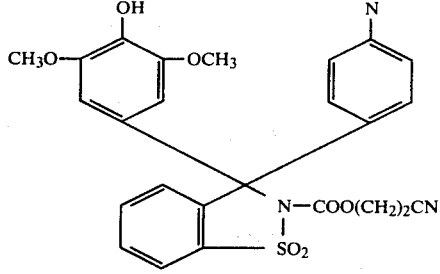 (13)

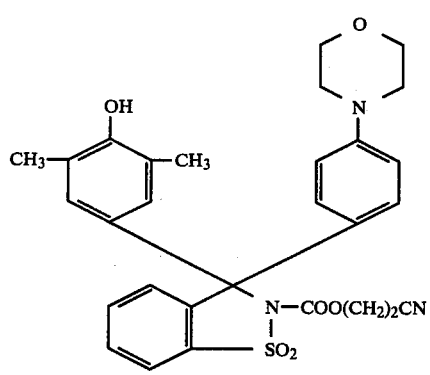 (14)
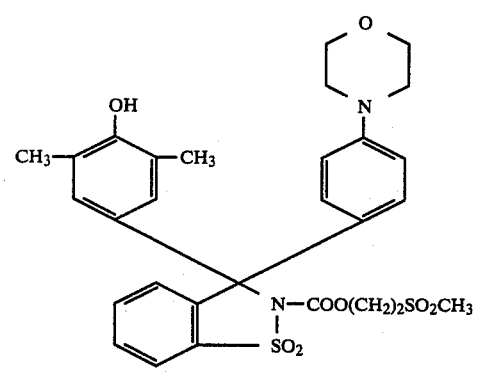 (15)
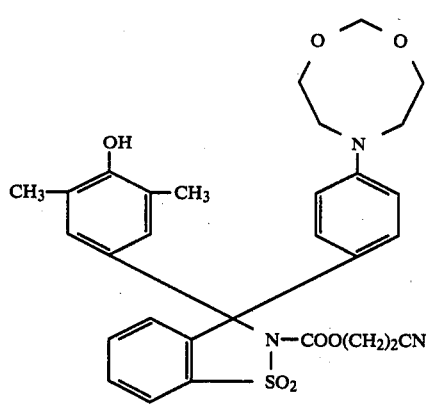 (16)
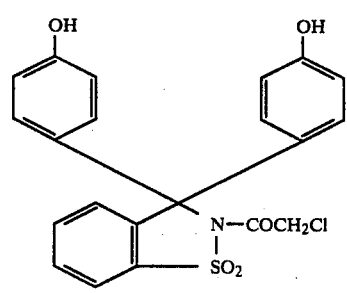 (17)
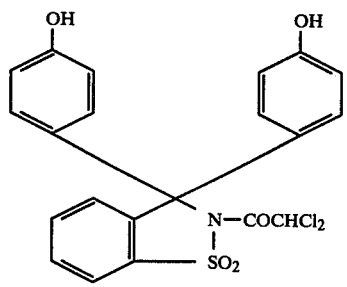 (18)
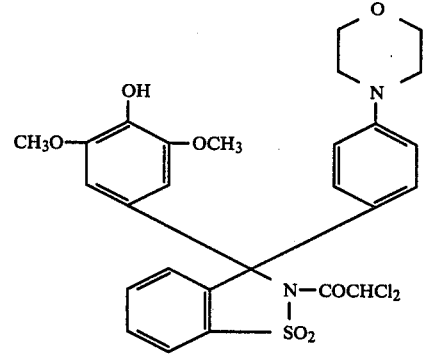 (19)
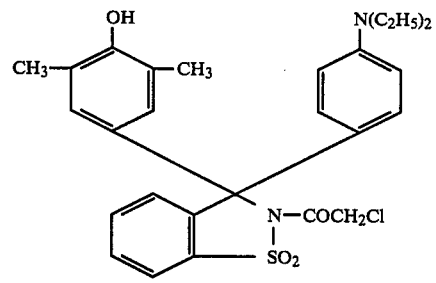 (20)
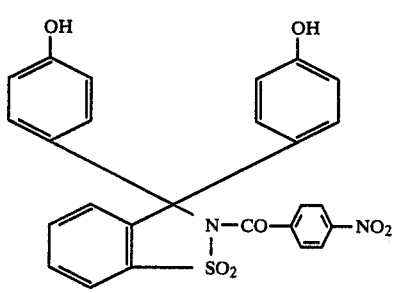 (21)
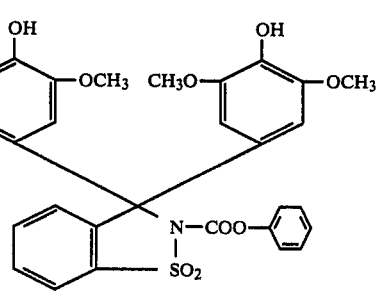 (22)

-continued
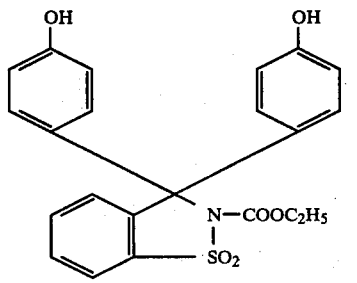 (23)
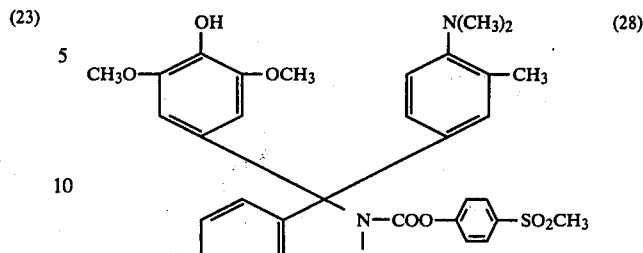 (28)
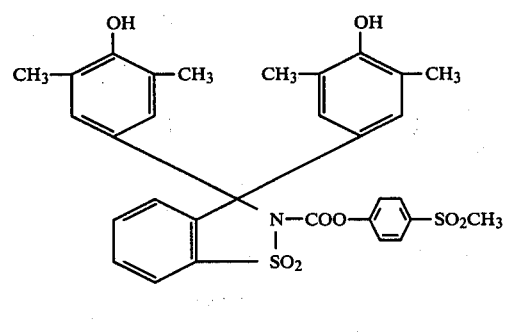 (24)
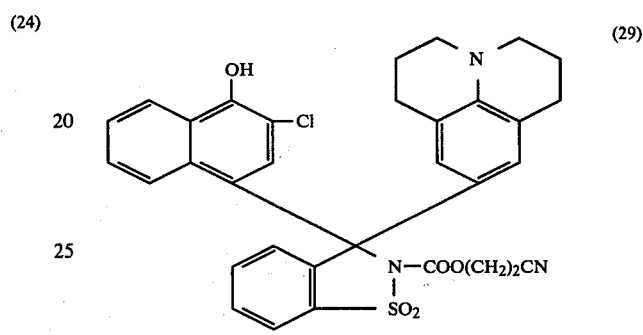 (29)
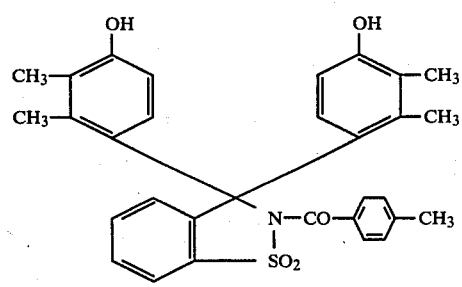 (25)
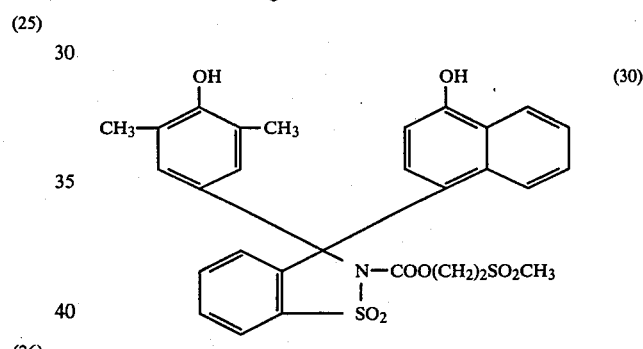 (30)
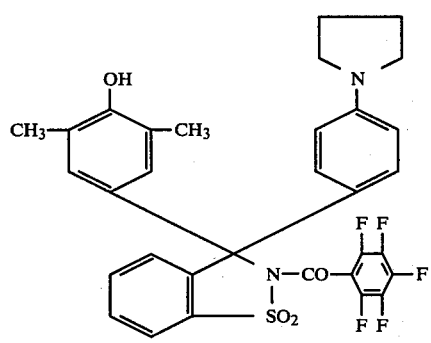 (26)
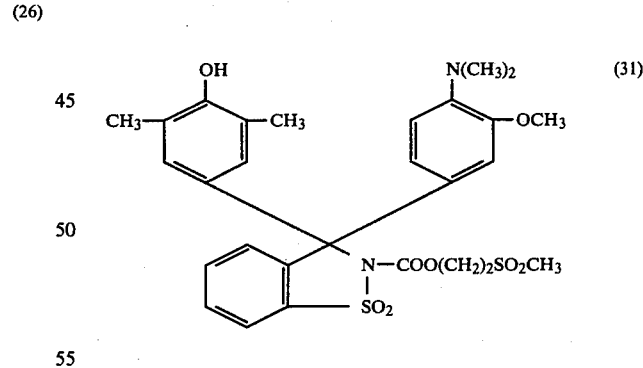 (31)
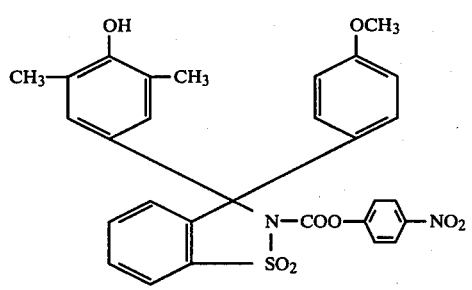 (27)
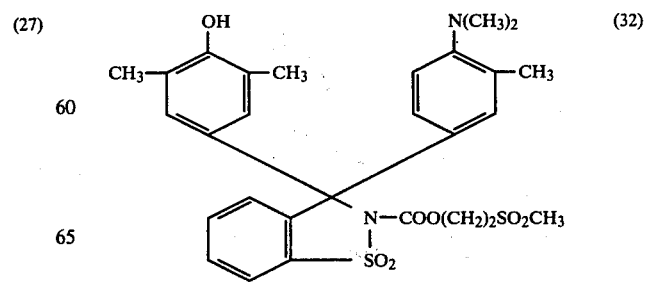 (32)

-continued
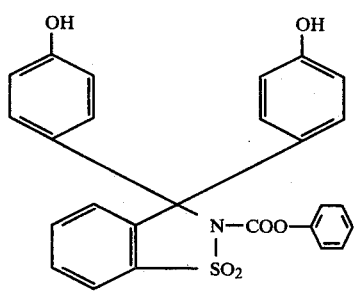 (33)
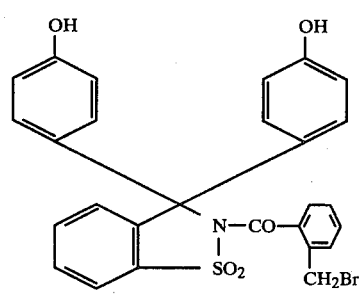 (34)
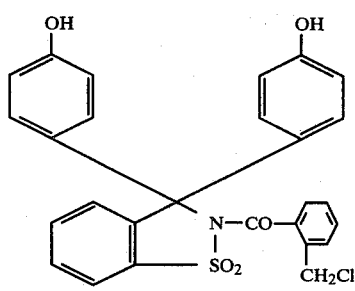 (35)
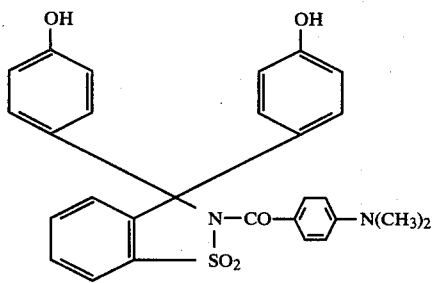 (36)
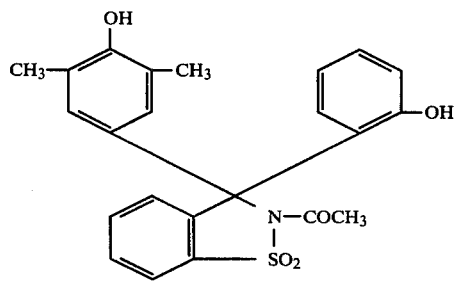 (37)
-continued
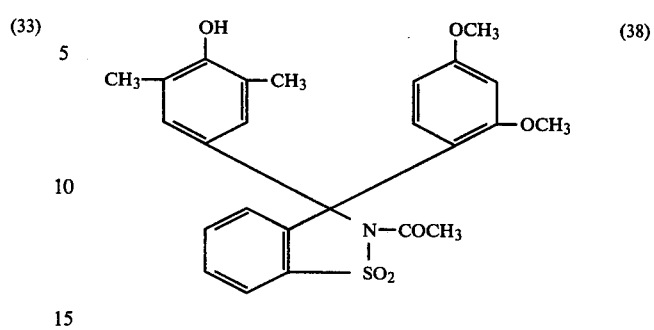 (38)
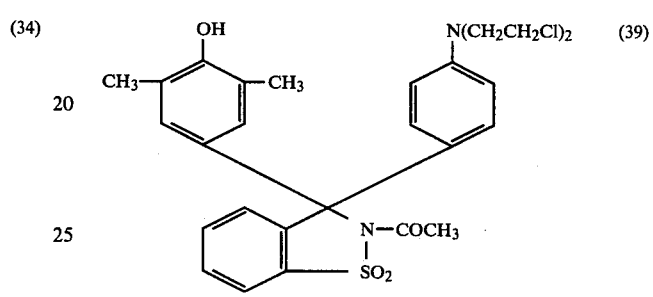 (39)
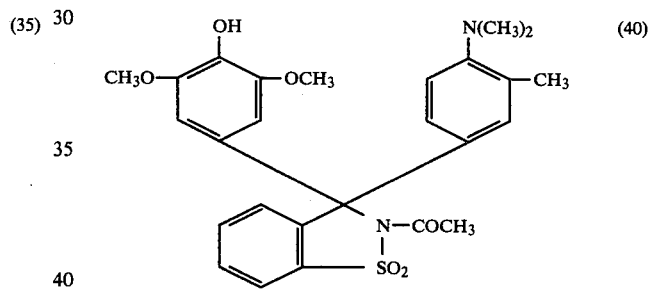 (40)
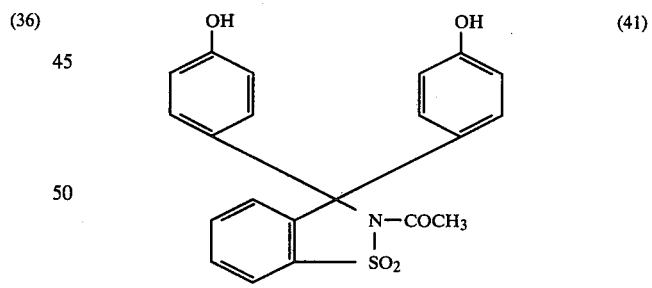 (41)
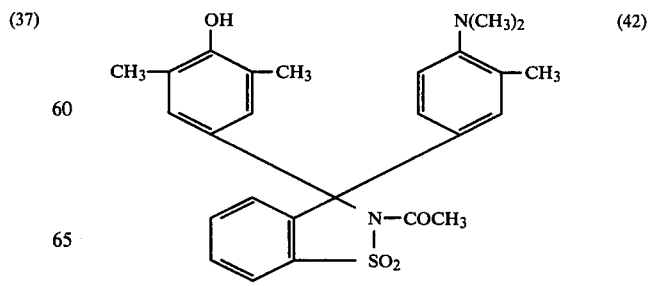 (42)

-continued
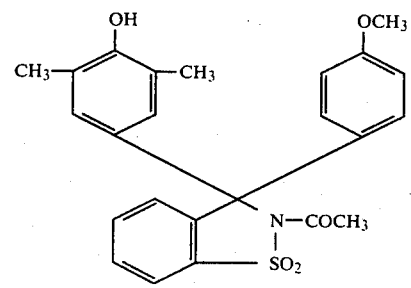 (43)
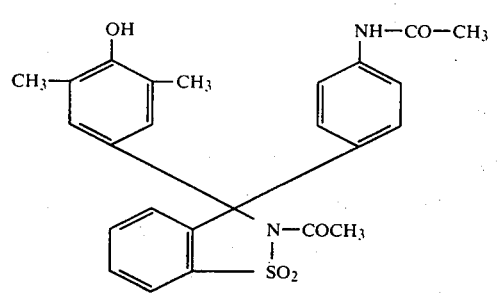 (44)
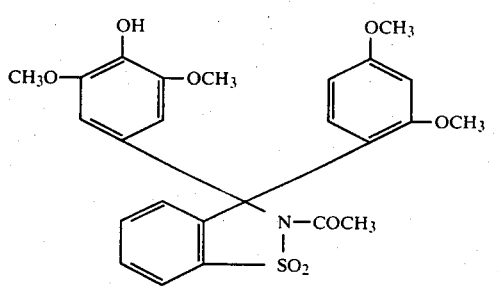 (45)
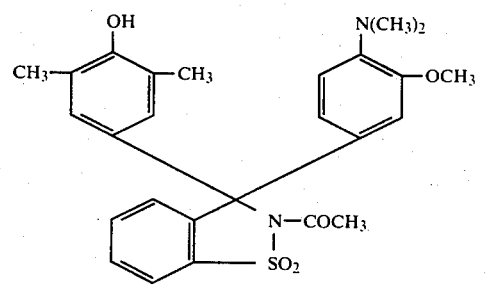 (46)
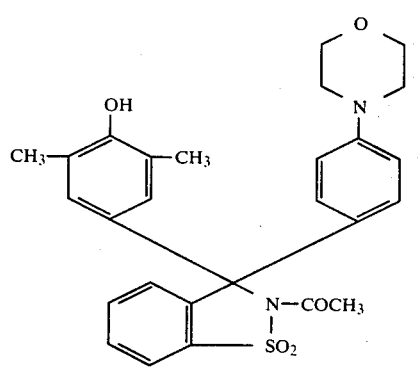 (47)
-continued
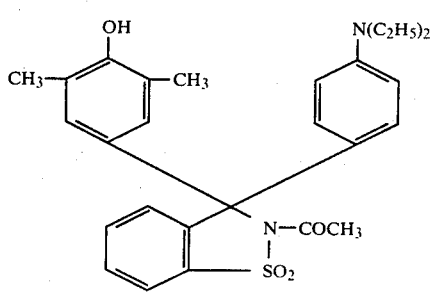 (48)
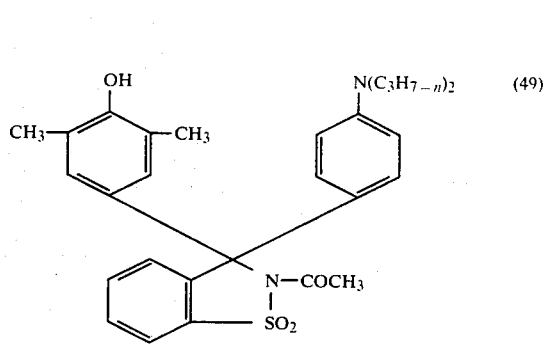 (49)
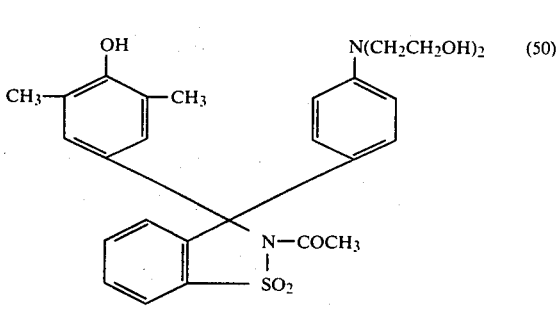 (50)
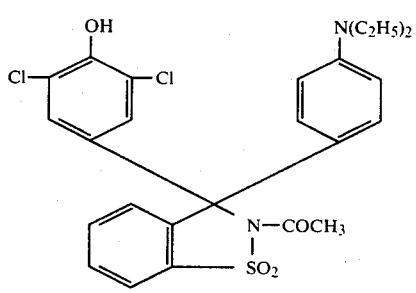 (51)
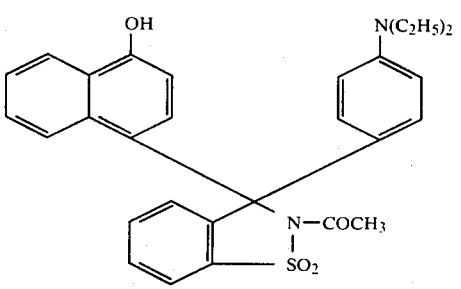 (52)

-continued

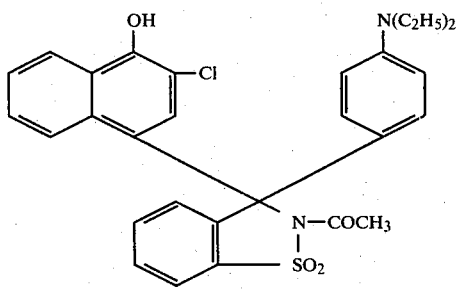 (53)

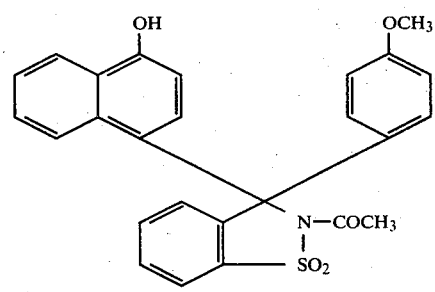 (54)

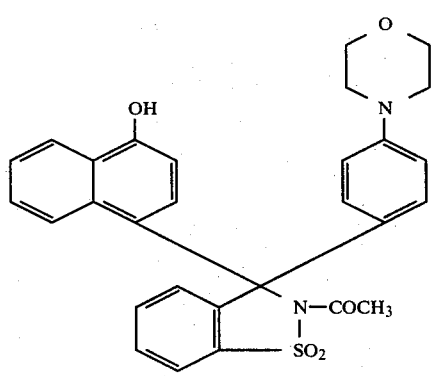 (55)

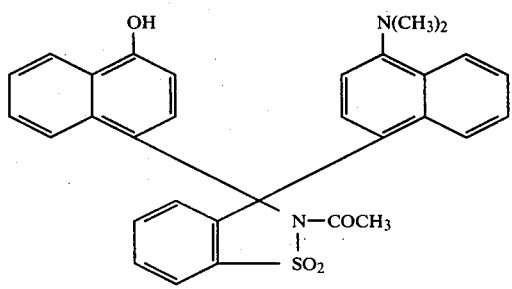 (56)

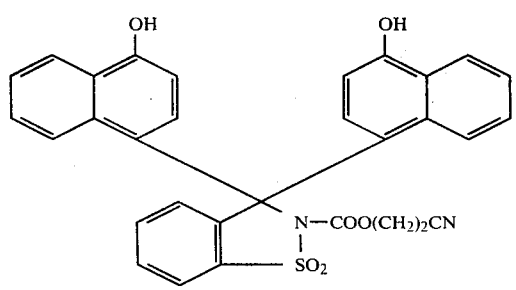 (57)

-continued

 (58)

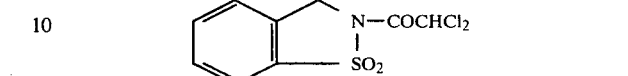 (59)

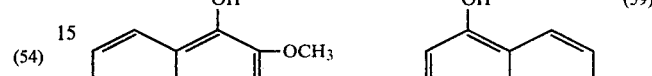

 (60)

As discussed above, the novel intermediates of the present invention are obtained as the products of the N-acylation step (1a) or (1b) and include the N-alkali metal salts produced in the first reaction of the N-acylation step (1b) and may be represented by the formula

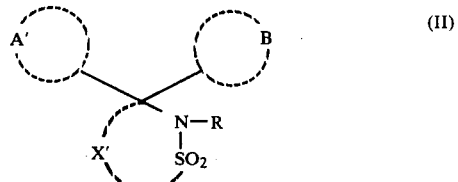 (II)

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety, unsubstituted or substituted with one or more substituents compatible with organometallic reagents, the same or different, or a naphthyl moiety, unsubstituted or substituted with one or more substituents compatible with organometallic reagents, the same or different; P is a protecting group; X' represents the atoms necessary to complete a 2,3-dihydrobenz[d]isothiazole-1,1-dioxide moiety or a 2,3-dihydronaphtho[1,8-de]-1,2-thiazine-1,1-dioxide moiety; and R is an alkali metal selected from sodium, potassium and lithium or a carbonyl moiety containing a

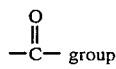

bonded to said N atom.

In a preferred embodiment, the novel intermediates of the present invention may be represented by the formula

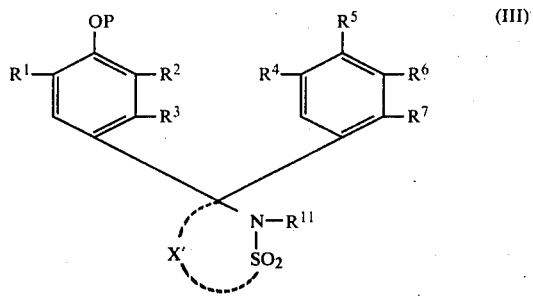  (III)

wherein P is a protecting group, $R^1$ and $R^2$ each are selected from hydrogen, alkyl, alkoxy, chloro and fluoro; $R^3$ is hydrogen, alkyl, alkoxy, or —OP; $R^2$ and $R^3$ taken together represent the carbon atoms necessary to complete a fused benzene ring; $R^4$ and $R^6$ each are selected from hydrogen, alkyl, alkoxy, chloro and fluoro; $R^5$ is hydrogen, alkyl, alkoxy, —$OP^I$ wherein $P^I$ is a protecting group, —N,N-(dialkyl)amino, —N,N-(w-$R^8$alkyl)$_2$amino wherein $R^8$ is halo or —$OP^{II}$ wherein $P^{II}$ is a protecting group, —NHCOCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring; $R^4$, $R^5$ and $R^6$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and $R^{11}$ is an alkali metal selected from sodium, potassium and lithium or $$-\overset{O}{\underset{\|}{C}}R^9$$

wherein $R^9$ is selected from from methyl, methyl substituted with at least one halo group selected from chloro, bromo and fluoro, alkoxy having 1 to 4 carbon atoms, phenyl, phenyl substituted preferably in the para position with alkyl having 1 to 4 carbon atoms or —N,N-(dialkyl)amino, phenyl substituted with at least one electron-withdrawing group, phenoxy, phenoxy substituted with at least one electron-withdrawing group, —O(CH$_2$)$_2$Y wherein Y is an electron-withdrawing group and phenyl substituted in the ortho position with —CH$_2$R$^{10}$ wherein R$^{10}$ is chloro or bromo.

Specific examples of intermediates of the present invention include:

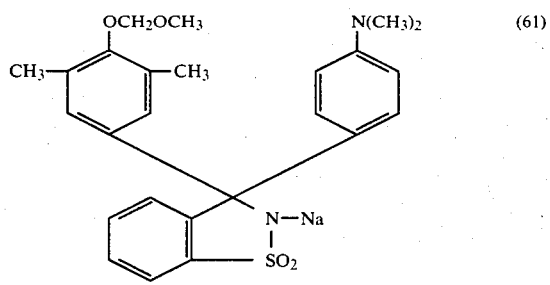 (61)

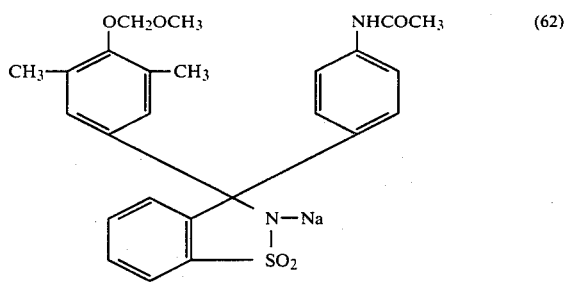 (62)

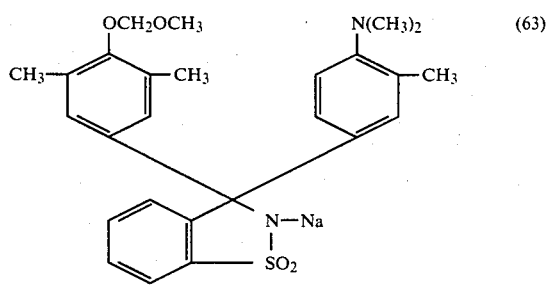 (63)

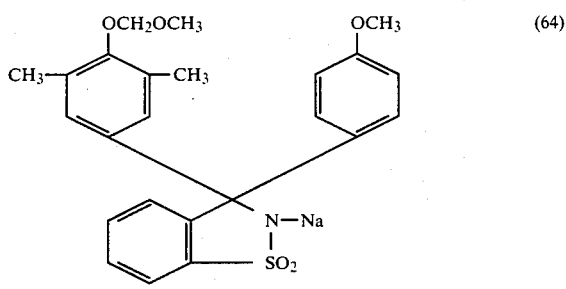 (64)

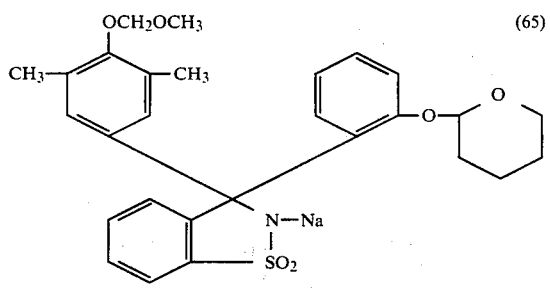 (65)

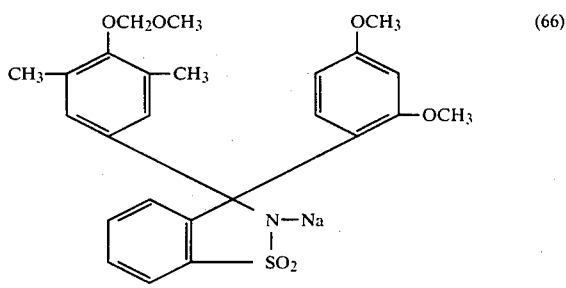 (66)

-continued
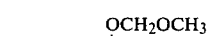

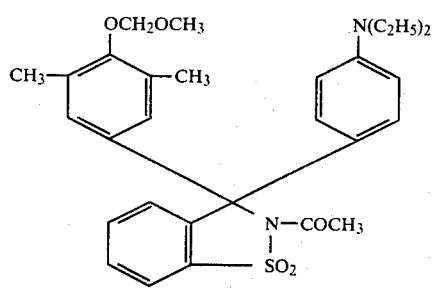 (77)
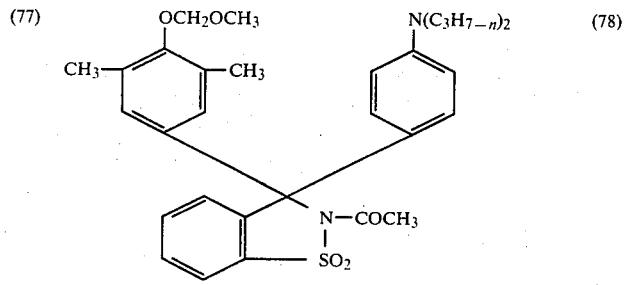 (78)
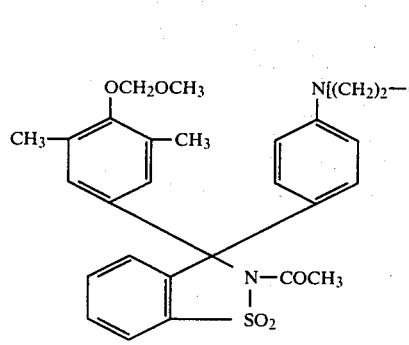 (79)
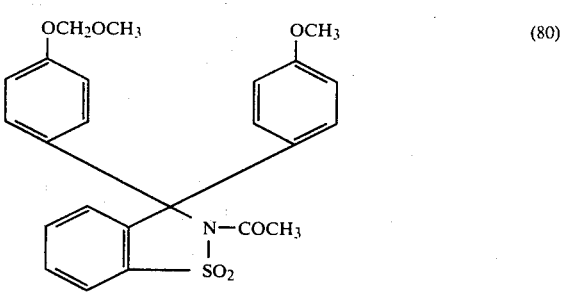 (80)
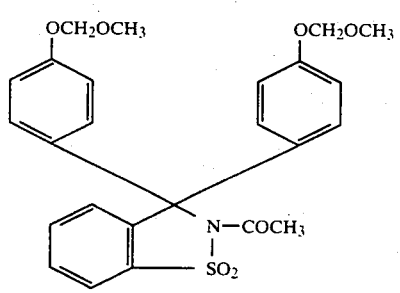 (81)
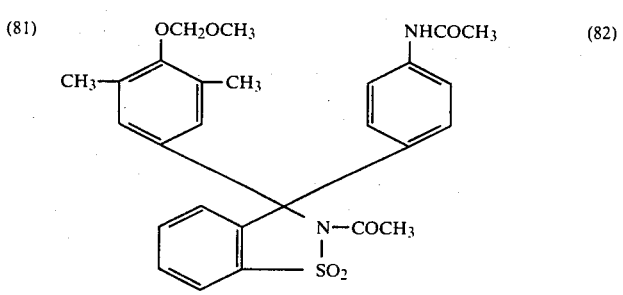 (82)
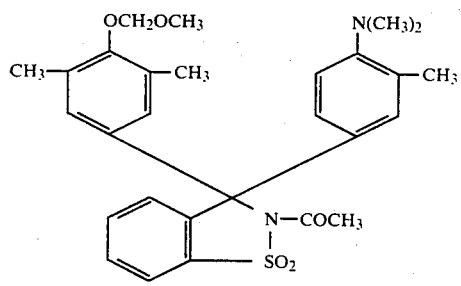 (83)
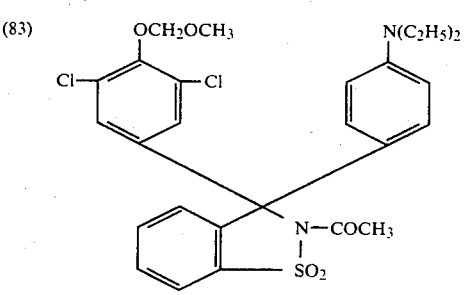 (84)
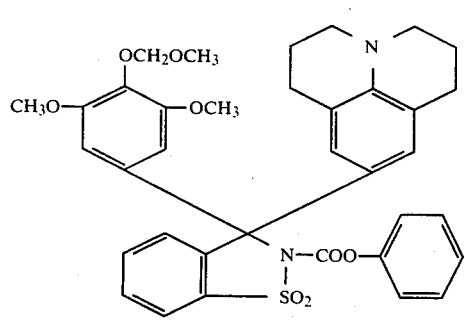 (85)
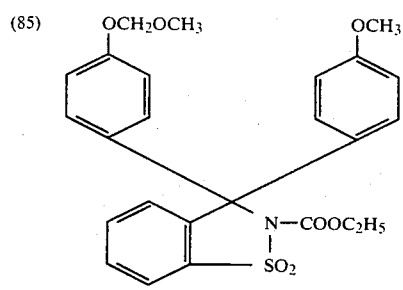 (86)

-continued
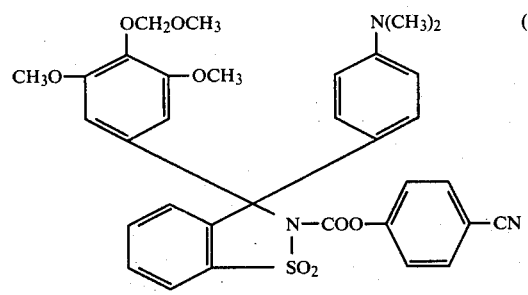 (87)
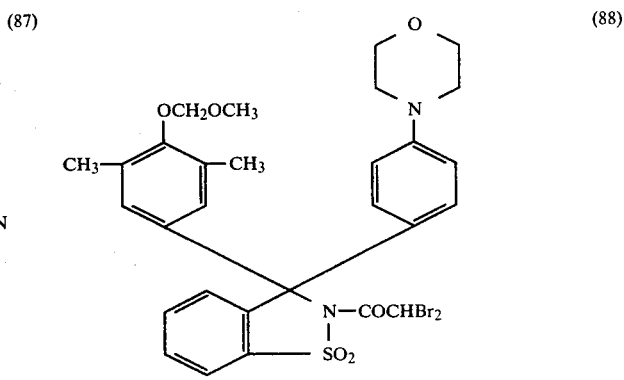 (88)
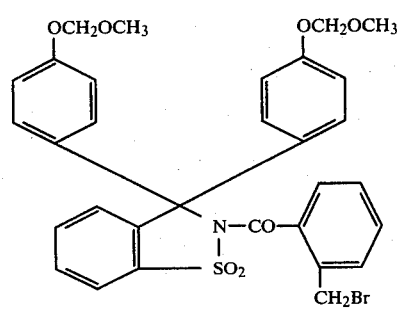 (89)
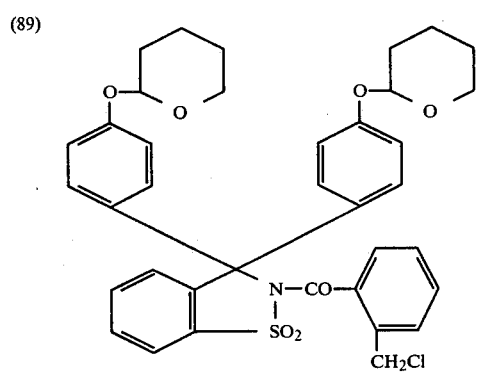 (90)
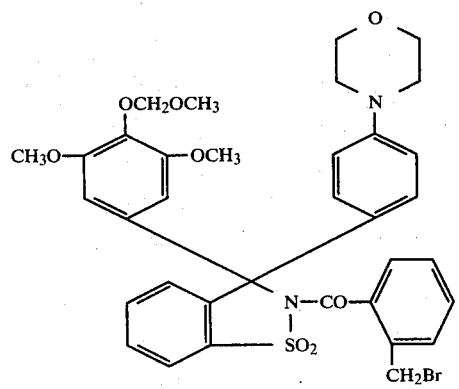 (91)
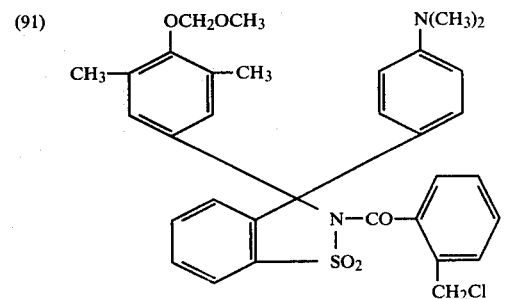 (92)
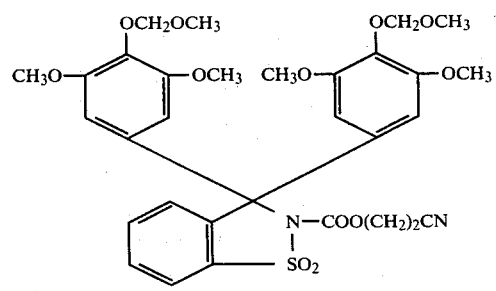 (93)
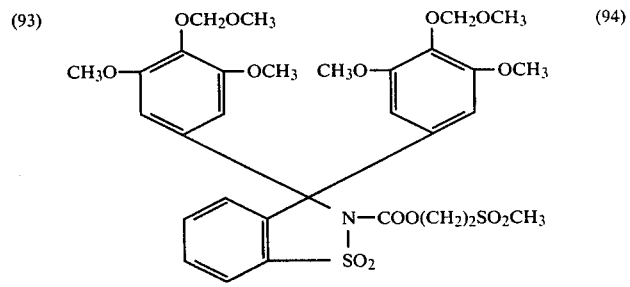 (94)

-continued
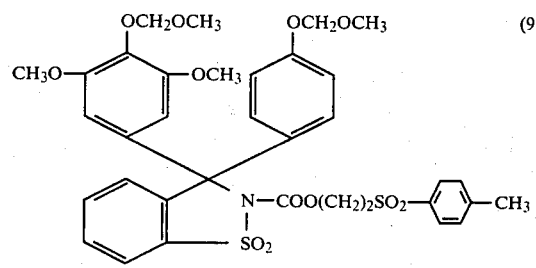 (95)
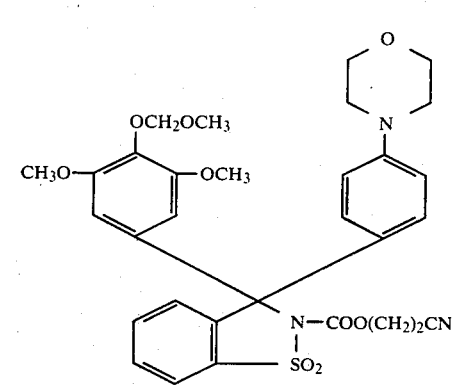 (96)
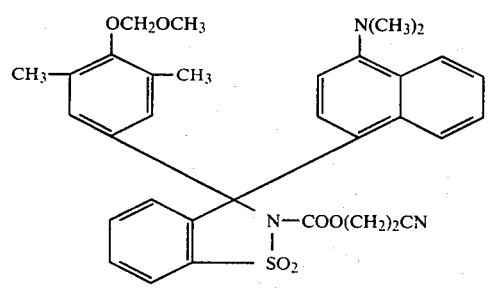 (97)
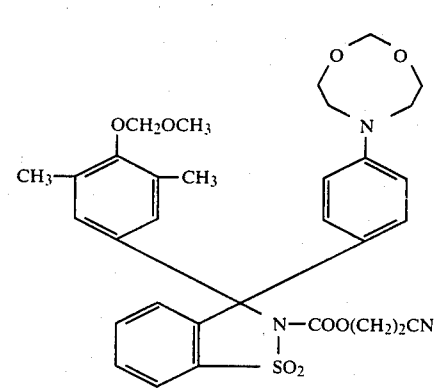 (98)
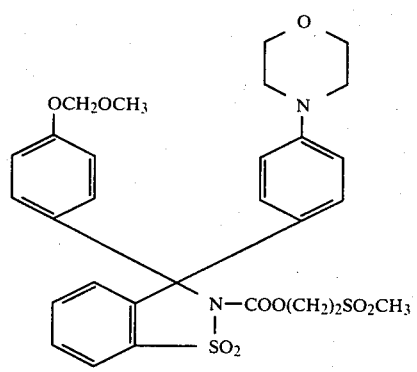 (99)
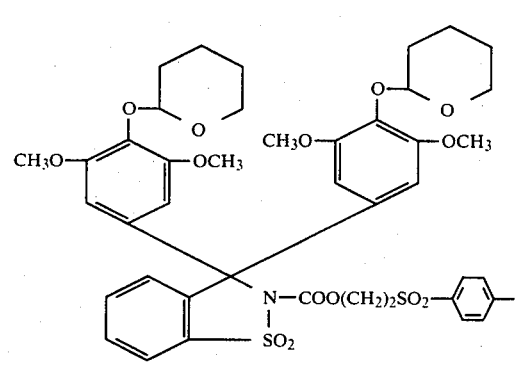 (100)
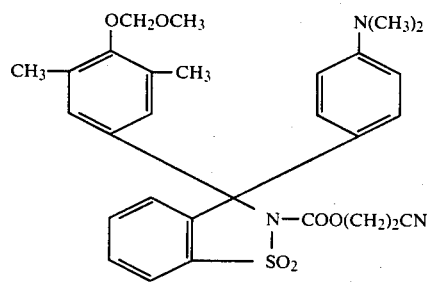 (101)
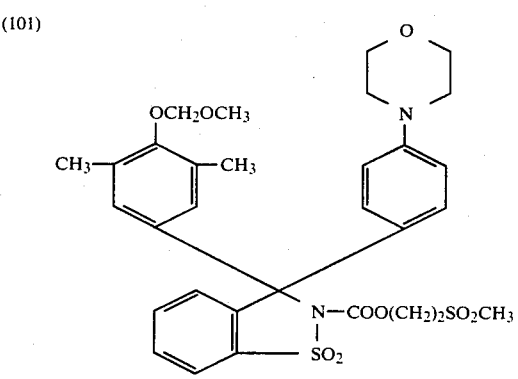 (102)

-continued
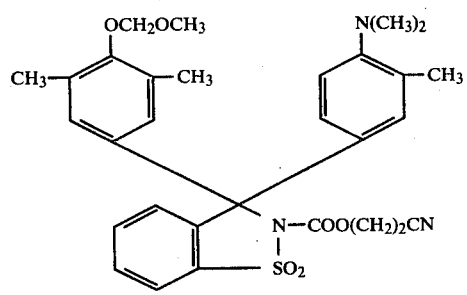 (103)
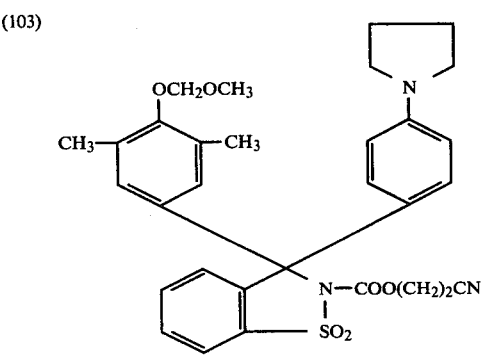 (104)
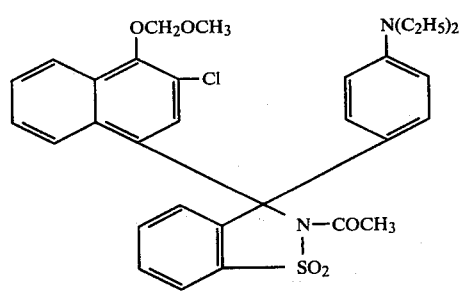 (105)
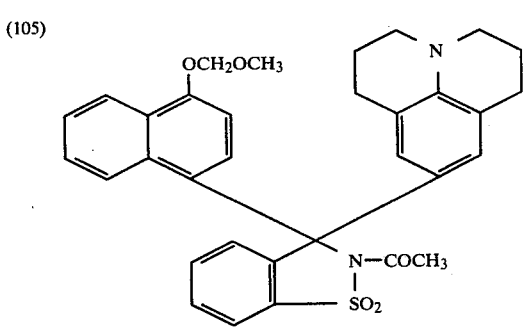 (106)
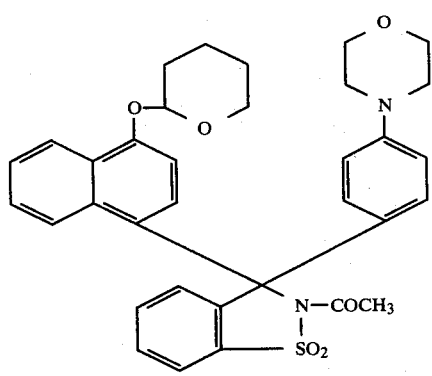 (107)
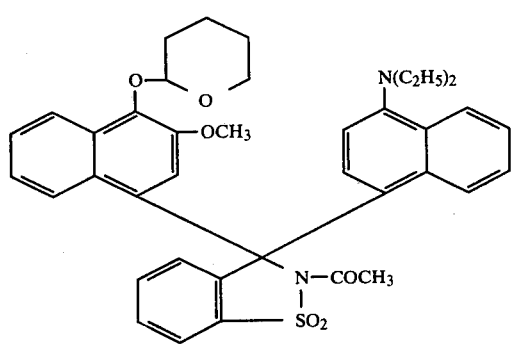 (108)
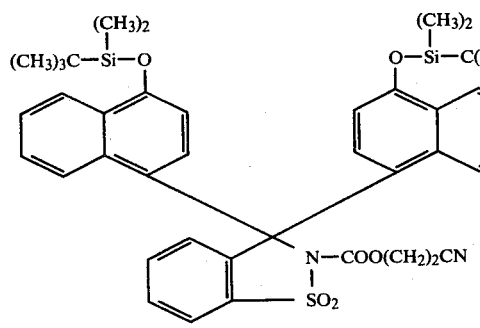 (109)
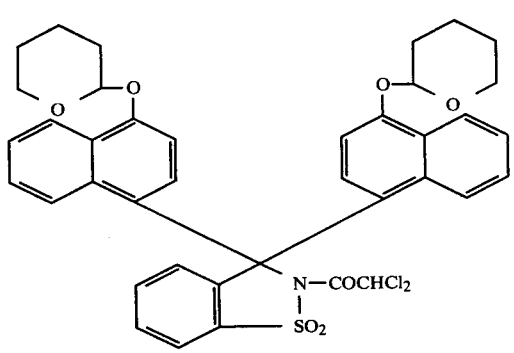 (110)

-continued

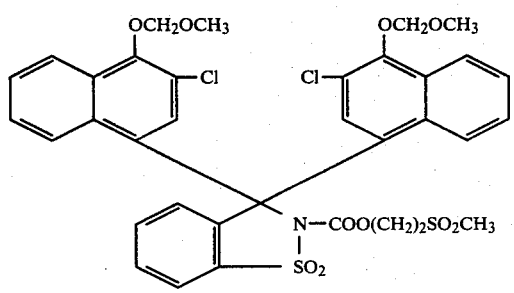
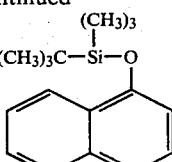
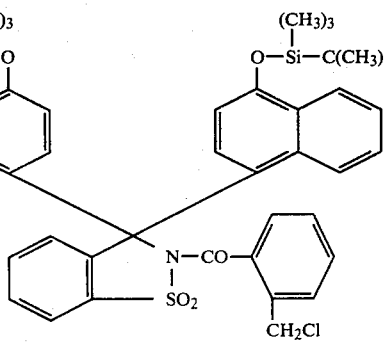
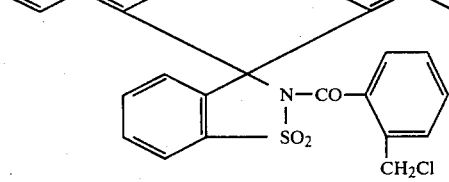

The 3-(4'-OP-1'-phenyl/4'-OP-1'-naphthyl)-3-(phenyl/naphthyl)-2,3-dihydrobenz[d]isothiazole-1,1-dioxides employed as starting materials in the above method may be synthesized by reacting a 3-(4'-OP-1'-phenyl/4'-OP-1'-naphthyl)benz[d]isothiazole-1,1-dioxide and a phenyllithium or a naphthyllithium reagent as disclosed and claimed in copending U.S. patent application Ser. No. 836,008 now abandoned to Alan L. Borror, Louis Cincotta, James W. Foley and Marcis M. Kampe filed concurrently herewith. As discussed therein, the 3-(4'-OP-1'-phenyl/4'-OP-B 1'-naphthyl)-benz[d]isothiazole-1,1-dioxides are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange resin using, for example, n-butyllithium. In preparing the Grignard reagent by reacting the blocked phenol or 1-naphthol with magnesium metal, the 4-halo substituent may be chloro, bromo or iodo. The Grignard or lithium reagent thus prepared is then reacted with saccharin, the N-lithium salt of saccharin or saccharin pseudo-chloride to yield the corresponding 3-(4'-OP-1'-phenyl/4'-OP-1'-naphthyl)benz[d]isothiazole-1,1-dioxide. Generally, the Grignard reagent is reacted with the pseudo-chloride, and the lithium reagent is reacted with the N-lithium salt. The 3-(4'-OP-1'-phenyl/4'-OP-1'-naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof.

To prepare the 3-(4'-OP-1'-phenyl/4'-OP-1'-naphthyl)-3-(phenyl/naphthyl)-2,3-dihydrobenz[d]isothiazole-1,1-dioxides, the 3-(4'-OP-1'-phenyl/4'-OP-1'-naphthyl)benz[d]isothiazole-1,1-dioxide is reacted with at least one molar equivalent of a phenyllithium or a naphthyllithium reagent in an inert organic solvent, such, as benzene, diethyl ether, dioxane, hexane, toluene, petroleum ether or tetrahydrofuran. The reaction temperature may vary over a relatively wide range from about −80° to 50° C. as may be readily determined for the particular reactants. For achieving maximum yields, the reaction generally is conducted at a temperature below about 0° C. and preferably between about −65° C. and −25° C.

The phenyl- or naphthyllithium reagent ultimately forming the B moiety of the subject intermediates and the ultimate products may be substituted or unsubstituted and may be prepared from the corresponding halo-substituted compound. For example, N,N-dimethylaniline may be halogenated to give the 4-halo compound which, in turn, is reacted with lithium metal or n-butyllithium to yield the 4-lithium compound. Halogenation may be carried out in a conventional manner using either chlorine or bromine, with or without a catalyst, or using N-bromosuccinimide or iodinemonochloride. When lithium metal is employed in the preparation of the 4-lithium compound, the halo substituent may be chloro, bromo or iodo and is either bromo or iodo when a lithium exchange reaction is employed. If substituents, such as, hydroxy, are present, they should be blocked with the appropriate protecting group to render them compatible with organometallic reagents prior to conversion to the 4-lithium compound. The protecting groups, of course, should be removable under mildly acidic conditions so that the substituents on the aryl moiety forming the B moiety can be regenerated simultaneously with the regeneration of the functional —OH group of the phenolic or naphtholic moiety, i.e., the A moiety.

The groups selected for protecting the functional phenolic or naphtholic hydroxy group and other hydroxy groups that may be present in the phenol or 1-naphthol should be stable to and compatible with organolithium and Grignard reagents and should protect the hydroxy group(s) against reaction under the conditions encountered in the synthesis of the aforesaid compounds and in the subsequent N-acylation step. In addition, the protecting group selected should be capable of being easily removed under weakly acid conditions to regenerate the hydroxy group(s) without the removal of or adversely affecting the N-carbonyl moiety or other substituents that may be present. Alkyl groups, such as methyl and ethyl, may be employed in those instances where they can be removed without removal of the N-carbonyl moiety. Because they can be readily removed without disturbing the N-substituent or other substituents, the phenol or 1-naphthol preferably is protected with methoxymethyl, 2'-tetrahydropyranyl or dimethyl-t-butylsilyl. The blocked phenols and 1-naphthols employing these protecting groups may be prepared by methoxymethylation as described, for example, by Kaoru Fuji et al, *Synthesis,* 4, pp. 276–277 (1975), by tetrahydropyranylation as described, for example, by William E. Parham et al, *J. Amer. Chem. Soc.,* 70, pp. 4187–4189 (1948) or by silylating with dimethyl-t-butylsilyl chloride in the presence of imidazole as described by E. J. Corey et al, *J. Amer. Chem. Soc.*, 94, pp. 6190–6191 (1972).

As noted above, hydroxy groups in addition to the functional —OH of the phenol and 1-naphthol may be blocked simultaneously with the functional hydroxy group, for example, by tetrahydropyranylation or methoxymethylation. Groups other than hydroxy that should be protected may be blocked prior to or subsequent to the blocking of the functional —OH. For example, carboxy group(s) may be protected by reacting a carboxy-substituted 4-halophenol (or 4-halo-1-naphthol) with 2-amino-2-methyl-1-propanol followed by blocking of the functional —OH. Sulfonamido (—NH—SO$_2$—R$^0$) and sulfamoyl (—SO$_2$—NH—R$^0$) substituents may be protected by a t-butyl group.

In accordance with the method of the present invention, the 3-(4'-OP-1'-phenyl/4'-OP-1'-naphthyl)-3-phenyl/naphthyl)-2,3-dihydrobenz[d]isothiazole-1,1-dioxides prepared as described above are reacted with a carboxylic acid halide,

wherein W and R$^9$ have the same meaning given above preferably in pyridine solution to give the corresponding

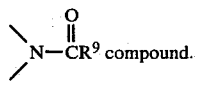 compound.

About 1 to 2 moles of acid halide are used for each mole of the isothiazole-1,1-dioxide. Since the reaction is exothermic, external heating may not be necessary, but the reaction mixture may be heated to facilitate completion of the reaction, if desired. Ordinarily, the reaction temperature ranges between about 0° and 100° C., and preferably, the reaction is conducted in an inert atmosphere, for example, under nitrogen.

The optional acylation step of the subject method is carried out by first reacting the isothiazole-1,1-dioxide with a molar equivalent and usually a slight excess of about 0.1 mole of an alkali metal hydride, MH, wherein M has the same meaning given above in an inert organic solvent at a temperature between about 0° and 100° C., preferably in an inert atmosphere, and then reacting the N-alkali metal salt thus formed with the said carboxylic acid halide,

Usually the acid halide is added to the reaction mixture containing the N-alkali metal salt. However, the N-alkali metal salt may be isolated prior to reaction with the acid halide, if desired. Solvents suitable for use in the alternate method of forming the

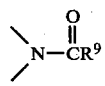

compound include dioxane, tetrahydrofuran, ethylether and benzene. The alkali metal, like the pyridine, affords substitution of the ring nitrogen of the ring-closing moiety in the acylation reaction.

Carboxylic acid halides are well known and may be prepared in a conventional manner, for example, by reacting the selected carboxylic acid, R$^9$COOH, with phosphorus trichloride, phosphorus pentachloride or thionyl chloride to give the corresponding R$^9$COCl, or by reacting the selected R$^9$OH with phosgene to give the corresponding ClCOOR$^9$.

Subsequent to the acylation step, the protecting group P is removed from the functional —OH by treating with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above. As indicated previously, any other protecting groups that may be present are removed simultaneously with the protecting group on the functional —OH.

The following examples are given to further illustrate the present invention and are not intended to limit the scope thereof.

EXAMPLE 1

Preparation of the compound having the formula:

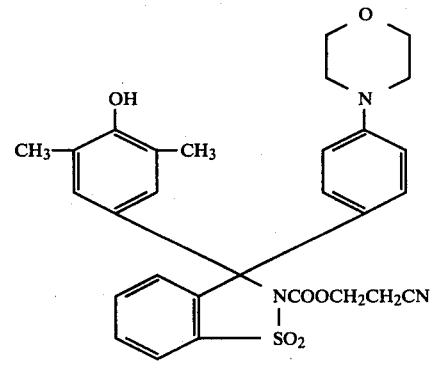

(a) N-(p-bromophenyl)morpholine (0.4 g.) was added to 20 ml. of tetrahydrofuran (THF) and the solution cooled to −65° C. To the solution was added 0.69 ml. of 2.4 M butyllithium in hexane with stirring and stirring was continued for 1 hour. (After 15 minutes the solution became cloudy and a white precipitate formed.) To this solution was added 0.5 g. of 3-(3',5'-dimethyl-4'-methoxymethoxy-1'-phenyl)benz[d]isothiazole-1,1-dioxide in 2 ml. THF at −65° C. under nitrogen. The resulting reaction mixture was a clear orange-yellow solution. The reaction mixture was stirred for 1 hour, poured into 100 ml. of water, made acidic with conc. hydrochloric acid (pH 6), and extracted with ether. The ether was dried over Na$_2$SO$_4$ and evaporated leaving an oil. The oil was taken up in ligroin (boiling range 30°–60° C.) and refluxed for 1 hour. The white solid that formed was collected to give 0.7 g. of 3-(3',5'-dimethyl-4'-methoxymethoxy-1'-phenyl)-3-(4''-N-morpholinyl-1''-phenyl)-2,3-dihydrobenz[d]isothiazole-1,1-dioxide having the formula:

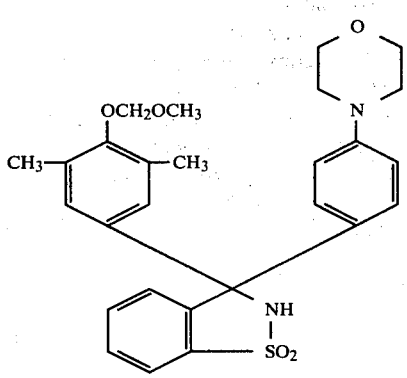

(b) The compound prepared in step (a) (0.7 g.) was placed in 20 ml. of pyridine under nitrogen and 0.15 ml. of β-cyanoethylchloroformate (ClCO₂CH₂CH₂CN) was added to the pyridine solution. The resulting reaction solution was stirred 1 hour, warmed gently and then poured into 100 ml. of water and extracted with chloroform. The chloroform was dried over Na₂SO₄, evaporated and the solid that formed was extracted with ligroin (boiling range 30°-60° C.). The solid obtained was the N-acylated compound, 3-(3',5'-dimethyl-4'-methoxymethoxy-1'-phenyl)-3-(4''-N-morpholinyl-1'''-phenyl)-2-(β-cyanocarbethoxy)-2,3-dihydrobenz[-d]isothiazole-1,1-dioxide having the formula:

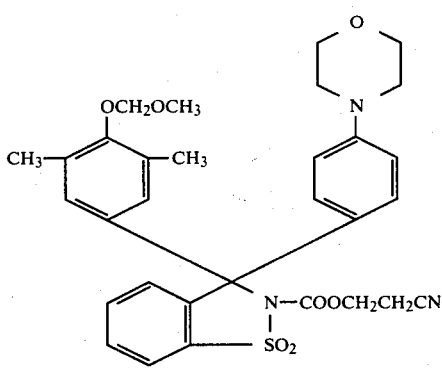

(c) The compound obtained in step (b) was then dissolved in methanol, made acidic with conc. hydrochloric acid and refluxed 1 hour. TLC from ether on silica gel showed 4 spots. The methanol solution was evaporated to leave 0.6 g. of solid. 200 mg. of solid in ether was placed on silica gel 1000 plates and the dark band was removed after drying plates. Aetone was used to remove the N-acylated product from the silica gel. The acetone was removed, ether added and the solution refluxed. The white solid that formed was recovered by filtration to give the title compound.

The 3-(3',5'-dimethyl-4'-methoxymethoxy-1'-phenyl)benz[d]isothiazole-1,1-dioxide having the formula:

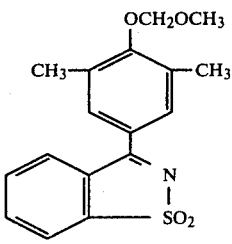

used in step (a) above was prepared as follows:

(i) Into a 2 liter three neck flask, fitted with a mechanical stirrer, nitrogen inlet and a dropping funnel, was placed 700 ml. of dry chloroform. The flask was immersed in an ice-water bath. Powdered phosphorus pentoxide (300.0 g.) was added to the vigorously stirred, cold chloroform. To this mixture was added over a 1 hour period a solution of 4-bromo-2,6-dimethylphenol (201.0 g.) in 400 ml. of dry dimethoxymethane. During this time the phosphorus pentoxide powder fused into an amorphous mass and stirring became difficult. TLC analysis (9:1 petroleum ether-ethyl acetate on silica gel) indicated that much unreacted starting phenol was still present. The temperature of the reaction mixture was allowed to rise to about 25° C. Additional 50 g. increments of phosphorus pentoxide were added to the stirred reaction mixture every 30-45 minutes until TLC analysis indicated the absence of starting phenol. The organic layer was decanted, washed with two 250 ml. portions of aqueous 10% sodium hydroxide and dried over calcium sulfate. The solvent was removed under reduced pressure leaving a pale yellow oil which was distilled from 25 g. of anhydrous potassium carbonate to give 220.0 g. of 4-bromo-2,6-dimethylmethylenemethoxyphenyl ether as a colorless oil (boiling point 112° C. and 0.5 mm Hg).

(ii) 4-Bromo-2,6-dimethyl-methylenemethoxyphenyl ether (85.04 g.; 0.347 mole) was dissolved in approximately 800 ml. of tetrahydrofuran. The solution was cooled to −75° C. under a nitrogen blanket, and 2.4 M n-butyllithium in hexane (144.8 ml; 0.346 mole) was added dropwise. Addition was completed within a 2 hour period giving a white slurry.

(iii) Saccharin (61.2 g; 0.334 mole) was dissolved in 600 ml. of dry tetrahydrofuran, and the solution was cooled to approximately −75° C. 2.4 M n-butyllithium in hexane (130.4 ml; 0.311 mole) was slowly added dropwise to the cooled solution under a nitrogen blanket. The temperature was not allowed to rise above −70° C. Addition was completed in about 90 minutes, giving a clear, very pale yellow solution.

(iv) The yellow solution obtained in step (iii) was slowly added (over a 3 hour period) to the white slurry obtained in step (ii) while keeping the temperature at −70° C. During this time the solids disappear giving a clear, caramel colored reaction mixture that first tends to darken with time and then gradually lightens. The reaction mixture was allowed to come to room temperature overnight and then was treated with 36.0 g. of ammonium chloride in 250 ml. of water, while cooling in an ice-water bath. The organic portion was decanted and dried over anhydrous calcium sulfate. The solvent was removed under reduced pressure to give a pink colored oil that became solid on standing in open air. The solid was recrystallized twice from 1-propanol, washed with a 60:40% mixture of petroleum ether-tetrahydrofuran and dried under vacuum to give 68.0 g. of the title compound as a white, crystalline solid.

3-(3',5'-dimethyl-4'-methoxymethoxy-1'-phenyl)-benz[d]isothiazole-1,1-dioxide also was prepared as follows:

Dry tetrahydrofuran (10-15 ml.) was added to magnesium turnings (0.20 g.) under nitrogen. A solution of 4-bromo-2,6-dimethyl-methylenemethoxyphenyl ether (2.0 g.) in tetrahydrofuran (30 ml.) was added gradually to the magnesium turnings with stirring and heating. After about twenty minutes of external heating to reflux, a self-sustaining reaction was observed. The remaining solution of phenyl ether was then added at a rate to maintain a comfortable reaction. Refluxing with external heating was continued after addition was complete and after one hour, the solution was cooled to room temperature and held under nitrogen. A solution of saccharin pseudo-chloride (1.89 g.) in tetrahydrofuran (40 ml.) was cooled to −78° C. and the previously prepared solution of magnesium bromide reagent was added dropwise to the pseudo-chloride solution under nitrogen. The resulting reaction mixture was stirred cold for about 2 hours and then stirred at room temperature overnight. The reaction mixture was then cooled in an ice water bath and treated with saturated aqueous ammonium chloride solution. The aqueous solution was extracted with chloroform several times and the combined chloroform extracts washed with water and dried over anhydrous sodium sulfate followed by drying over anhydrous calcium sulfate. Upon removing the chloroform, a colorless oil was obtained which was extracted several times with small portions of light petroleum ether to leave behind a pale yellow tacky tar. The yellow tar was treated with ether leaving behind an off-white solid. The off-white solid was dissolved in a small amount of chloroform, treated with carbon black and filtered through Celite. Upon removing the solvent, the title compound was obtained as an off-white solid which was dried under vacuum in the presence of $P_2O_5$. Yield 0.520 g.

3-chlorobenz[d]isothiazole-1,1-dioxide (saccharin pseudo-chloride) was prepared as follows:

35 g. of saccharin and 43.7 g. of $PCl_5$ were heated at 170° C. for 1½ hours during which time complete solution occurred and $POCl_3$ began to reflux. The $POCL_3$ was removed at reduced pressure to leave a crystalline residue. Diethyl ether was added to the crystalline residue and stirred well. The title compound was recovered as white crystals, 12.5 g. (melting range 146°-147° C.).

The N-(p-bromophenyl)morpholine having the formula

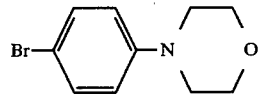

used in step (a) above was prepared as follows:

25 g. of N-phenylmorpholine was dissolved in 200 ml. of carbon tetrachloride and stirred well. To this was added all at once 27.2 g. of N-bromosuccinimide. There was an exotherm to 45° C. The reaction solution was stirred until the temperature began to decrease and then was heated to reflux for 3 hours. TLC on silica gel with 3/2 petroleum ether/ether indicated that the reaction was complete. The reaction solution was then cooled, the succinimide removed by filtration and the solution evaporated to yield a yellow solid. The solid was dissolved in 250 ml. of ethanol and cooled to give 22 g. of the title compound as white crystals.

The β-cyanoethylchloroformate having the formula ($CNCH_2CH_2COOCl$) used in step (b) above was prepared as follows:

To 100 ml. of dry benzene, cooled in an ice bath, was added phosgene gas until 34.0 g. was collected. Hydroxyacrylonitrile (20.2 g.) was added to the cooled phosgene solution. (The temperature rose slightly to approximately 8° C.) The resulting heterogeneous mixture was cooled to 3° C. with stirring, and pyridine (22.6 g.) in 25 mls. of benzene was added dropwise. Heat was evolved, and the temperature was not allowed to rise above 10° C. Very vigorous stirring was maintained until solid began to form. After about 1 hour, the reaction mixture was stirred at approximately 5° C. for 15 minutes, then allowed to come to 15° C.–20° C. and stirred for another 15 minutes. The reaction mixture was then cooled to 5° C. and 26 ml. of ice water was added in increments. The solids dissolved with liberation of heat and evolution of gas. The temperature was not allowed to rise above 15° C. over the next 15–20 minutes. The reaction mixture was then stirred at room temperature for 2 hours, the benzene layer decanted and dried over anhydrous $Na_2SO_4$, followed by drying over anhydrous $CaSO_4$. The solvent was removed under reduced pressure to yield an almost colorless oil which was redistilled under vacuum at a boiling range of 68.5°–70.5° C. (pot temperature 98°–103° C.) to yield 18.2 g. of the title compound as a colorless oil.

EXAMPLES 2 AND 3

The compounds having the formulas

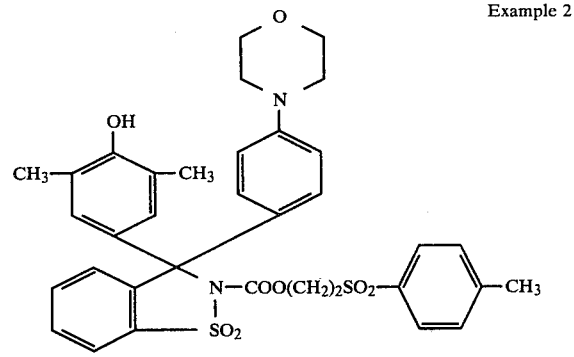

Example 2

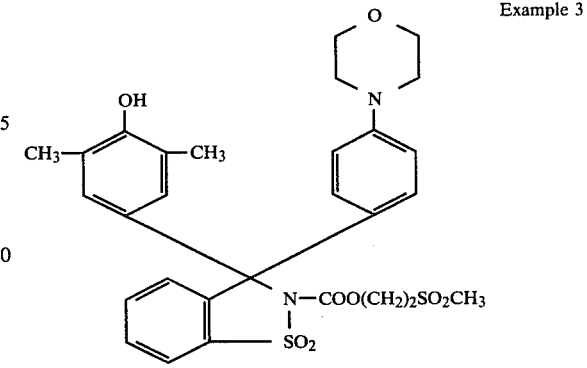

Example 3 were prepared in the same manner described in Example 1 except that the 3-(3',5'-dimethyl-4'-methoxymethoxy-1'-phenyl)-3-(4''-N-morpholinyl-1''-phenyl)2,3- dihydrobenz[d]isothiazole-1,1-dioxide was reacted in step (b) with the appropriate acylating agents, namely,

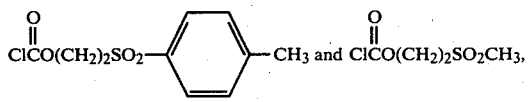

to yield the corresponding N-acylated compounds which were treated as in step (c) above to remove the protecting groups.

EXAMPLE 4

Preparation of the compound having the formula

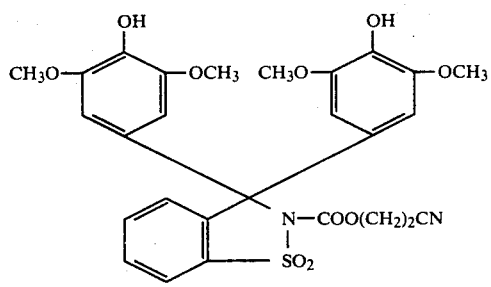

(a) 55 g. of 4-bromo-2,6-dimethoxy-methylenemethoxyphenyl ether was dissolved in 300 ml. of anhydrous tetrahydrofuran under a stream of nitrogen. The solution was cooled to $-65°$ C. during which time some of the phenyl ether precipitated. To this was added 79 ml. of butyl-lithium (2.4 M in hexane) at a range to keep the temperature below $-50°$ C. The resulting solution was cooled to $-65°$ C. and was stirred for 30 minutes. To this solution was added 19 g. of saccharin pseudochloride in two portions so as to keep the temperature below $-40°$ C. The reaction solution was cooled to $-65°$ C. and was stirred for 40 minutes. TLC showed one main spot on silica gel with 10 ml. ether/2 drops methanol. The reaction solution was poured into 2000 ml. of water and made acidic to pH 6. The mixture changed color from orange to yellow at this pH. The mixture was extracted two times with ether (2 liters) and the ether washed with water. The ether was dried over sodium sulfate and evaporated to leave a light yellow solid. The solid was recrystallized from 450 ml. of n-propanol to give 42 g. of 3,3-di(3',5'-dimethoxy-4'-methoxymethoxy-1'-phenyl)-2,3-dihydrobenz[d]isothiazole-1,1-dioxide as off-white crystals (melting range 151.5°–152.5° C.).

(b) The compound prepared in step (a) (27.0 g.) was dissolved in 125 ml. of dioxane at room temperature under nitrogen. To this solution was added 2.50 g. of NaH (57% oil dispersion) and the resulting dispersion stirred for 45 minutes. (Evolution of hydrogen was observed.) Then 8.0 ml. of ClCOOCH$_2$CH$_2$CN was added and an exotherm resulted. The resulting reaction mixture was stirred for 3 hours. The initial yellow color disappeared and a white dispersion formed. The dispersion was poured into 2 liters of water, made neutral with dilute HCl and extracted with chloroform. The chloroform was washed with water, separated, dried over sodium sulfate, and evaporated to yield a white solid. The solid was stirred with ethyl ether, isolated by filtration, dried in vacuo, and crystallized from methanol. The white needles that formed were recovered by filtration to give the >N-COOCH$_2$CH$_2$CN derivative of 3,3-di(3',5'-dimethoxy-4'-methoxymethoxy-1'-phenyl)-2,3-dihydrobenz[d]isothiazole-1,1-dioxide.

(c) 3.7 g. of 3,3-di(3',5'-dimethoxy-4'-methoxymethoxy-1'-phenyl)-2-β-cyanocarbethoxy-2,3-dihydrobenz[d]isothiazole-1,1-dioxide prepared as in step (b) above was placed in 200 ml. of methanol and 2 drops of HCl were added. The resulting solution was refluxed and the reaction was followed by TLC on silica gel with ether. When TLC indicated that no more blocked compound remained, the reaction was discontinued and the methanol removed in vacuo to leave an egg-white solid (3.2 g.). This was dissolved in 80 ml. of 1,2-dichloroethane with heating and 80 ml. of petroleum ether was added with swirling. The solution was cooled and the light beige crystals that formed were collected and dissolved in 175 ml. of ethanol at reflux. The ethanol solution was allowed to cool in the refrigerator overnight and 2.7 g. of the title compound was collected as white needles (melting range 191°–193° C.).

The methoxymethylation of 4-bromo-2,6-dimethoxyphenol used in step (a) above was carried out as follows:

To a 3 liter flask was added 300 g. of P$_2$O$_5$ under nitrogen and 800 ml. of chloroform (previously dried over P$_2$O$_5$). The mixture was cooled to $-15°$ C. with a dry-ice acetone bath and then 50 g. of 4-bromo-2,6-dimethoxyphenol in 800 ml. of dimethoxymethane was added over a 25 minute period while maintaining the temperature at $-15°$ C. or below. To the resulting reaction mixture was added 1 ml. of conc. sulfuric acid and then the temperature was allowed to come to room temperature. During this time, a tacky mass of P$_2$O$_5$ developed. The reaction mixture was stirred for 3 hours. TLC indicated that the reaction was complete. The chloroform was then decanted into 400 ml. of 10% aqueous sodium hydroxide, stirred well and the chloroform layer separated, washed with water, dried over Na$_2$SO$_4$ and evaporated to leave light tan crystals. n-Propanol was added to the crystalline residue, stirred and filtered to give 32.7 g. of the title compound as white crystals (melting range 98°–100° C.).

EXAMPLES 5 AND 6

The compounds having the formulas

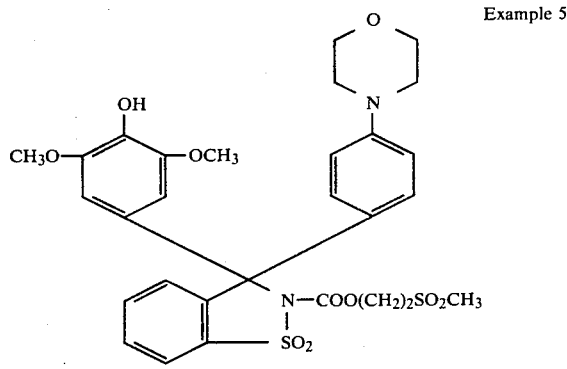

Example 5

Example 11

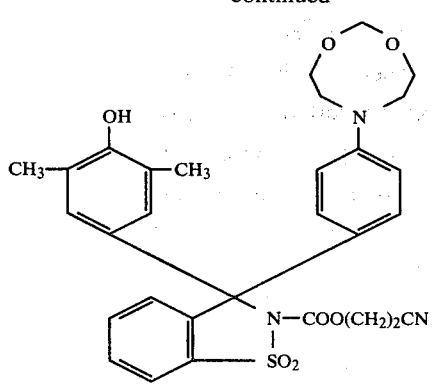

were prepared according to the procedure given in Example 1 except that in step (a) the 3-(3',5'-dimethyl-4'-methoxymethoxy-1'-phenyl)benz[d]isothiazole-1,1-dioxide was reacted with the appropriate lithium reagent, namely,

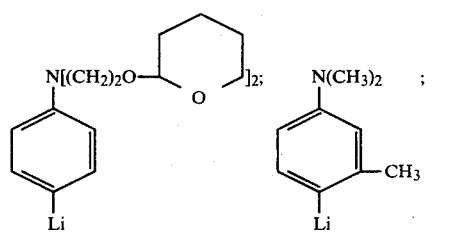

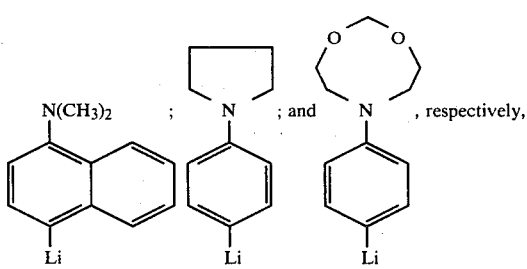

and the 2'-tetrahydropyranyl groups were removed from the protected N,N-di(β-hydroxyethyl)anilino moiety of Example 7 in step (c) simultaneously with the 4'-methoxymethyl protecting group.

N-(p-Li-phenyl)tetrahydro-2H,4H-1,3,6-dioxazocine may be prepared by reacting the corresponding p-halophenyl compound with n-butyllithium. The N-(p-halophenyl)tetrahydro-2H,4H-1,3,6-dioxazocines are prepared by reacting p-halo-N,N-di(β-hydroxyethyl)aniline with certain dihalomethanes in the presence of a solid alkali metal hydroxide or concentrated aqueous solution thereof and a quaternary ammonium salt. These compounds and their preparation form the subject matter of U.S. patent application Ser. No. 836,066, now U.S. Pat. No. 4,172,083, of Louis Cincotta, James W. Foley and Marcis M. Kampe filed concurrently herewith.

Tetrahydropyranylation of p-Br-N,N-di(β-hydroxyethyl)aniline was carried out as follows:

p-Br-N,N-di(β-hydroxyethyl)aniline (20.0 g.) was dissolved in 475 ml. of dichloromethane containing 60 ml. of dihydropyran. To this solution was added 1 ml. of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g. of the title compound.

The corresponding 4-Li compound was prepared by dissolving 4-bromo-N,N-di(β-2'-tetrahydropyranyloxyethyl)aniline (10.0 g.) in 100 ml. of tetrahydrofuran, cooling the solution to −65° C. and adding 10 ml. of n-butyllithium (2.4 M in hexane) under nitrogen at a rate to maintain the temperature at −65° C.

EXAMPLES 12-14

The compounds having the formulas

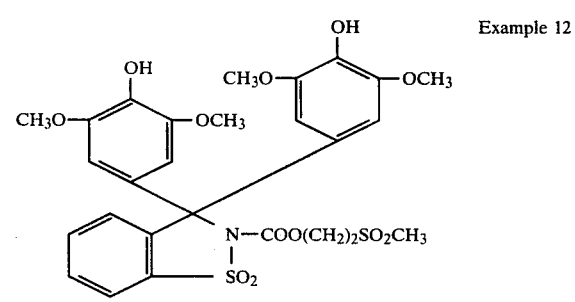

Example 12

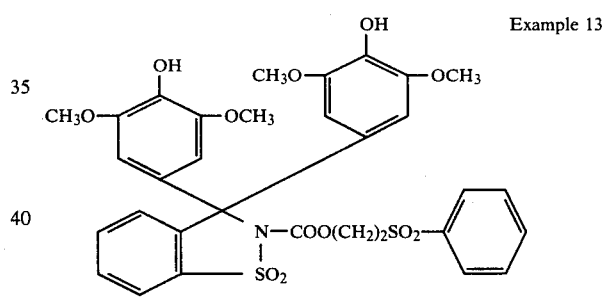

Example 13

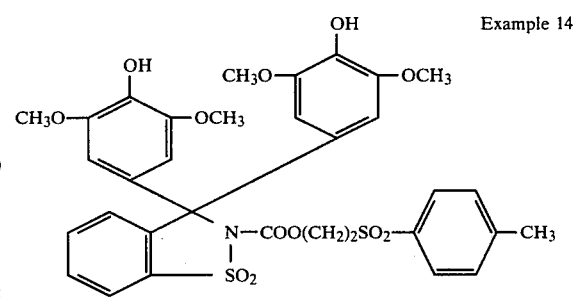

Example 14 were prepared in the same manner described in Example 4 except that the acylating agents employed were

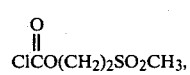
ClCO(CH₂)₂SO₂CH₃,

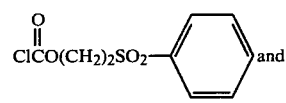 and

Example 6

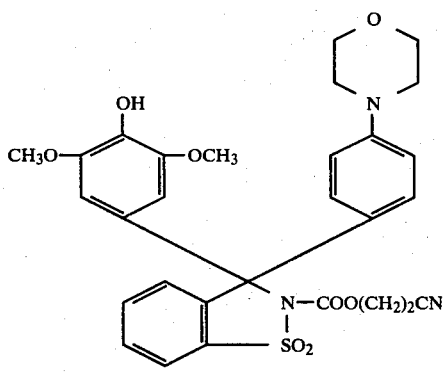

were prepared according to the procedure described in Example 1 except that 3-(3',5'-dimethoxy-4'-methoxymethoxy-1'-phenyl)benz[d]isothiazole-1,1-dioxide was used in the reaction of step (a) and the appropriate acylating agents, namely,

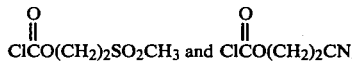

were used in step (b).

The 3-(3',5'-dimethoxy-4'-methoxymethoxy-1'-phenyl)benz[d]isothiazole-1,1-dioxide used in step (a) above was prepared as follows:

(i) Using an 18 gauge needle-syringe, 20.0 mls. of n-butyllithium (2.4 M in hexane) was added dropwise over 1 hour to a solution of 9.16 g. of saccharin (previously dried overnight at 80° C. in vacuo) in 250 mls. of dry tetrahydrofuran under nitrogen at −75° C. to −73° C. with rapid stirring. The reaction solution comprising the N-lithium salt of saccharin in tetrahydrofuran was used directly in step (iii) without isolating the lithium salt.

(ii) In a dried 1 l. flask, 13.86 g. of 4-bromo-2,6-dimethoxy-methylenemethoxyphenyl ether was dissolved in 300 mls. of dry tetrahydrofuran under nitrogen, and 20.83 mls. of n-butyllithium (2.4 M in hexane) was added dropwise with stirring at −75° C. After addition was complete, the reaction solution was stirred at −75° C. for about 30 minutes.

(iii) The solution of saccharin lithium salt prepared in step (i) was transferred to an addition funnel using a double-tip needle under nitrogen pressure and added to the solution of 4-Li-2,6-dimethoxy-methylenemethoxyphenyl ether prepared in step (ii) over about 15 minutes with stirring at a temperature of −75° C. to −70° C. The reaction mixture was stirred for about 2 hours at −75° C. and then warmed to 0° C. during an hour.

(iv) A solution of 5.2 g. of ammonium chloride in 175 mls. of water was added dropwise to the reaction mixture of step (iii) and the reaction mixture was transferred to a 1 l. separatory funnel. After the two phases separated, the aqueous phase was removed and the pH was lowered from about 11 to about 6-7 by the dropwise addition of aqueous 5% hydrochloric acid solution. (A color change from yellow to colorless was observed.) The aqueous phase was returned to the separatory funnel, partitioned and the aqueous phase again separated and then extracted with fresh ether (100 mls.). The ether and tetrahydrofuran/hexane extracts were combined, dried over magnesium sulfate overnight, filtered and the solvent removed to leave a yellow oil which crystallized. Ether (100 mls.) was added to the crystalline material and the crystalline material was ground under ether in a mortar, filtered, washed with more ether followed by petroleum ether and air dried. A second crop was collected from the filtrate to give a total yield of 13.0 g. of the title compound.

EXAMPLES 7-11

The compounds having the formula:

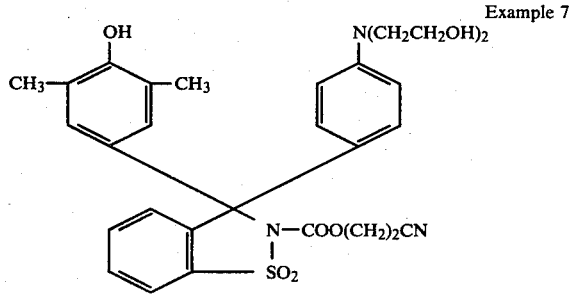

Example 7

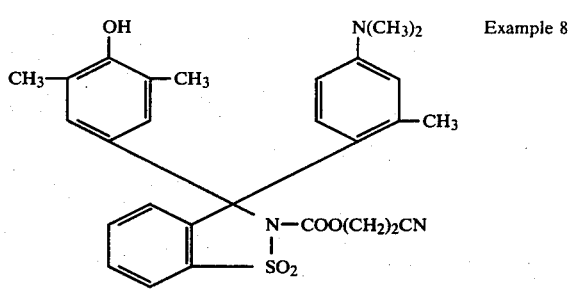

Example 8

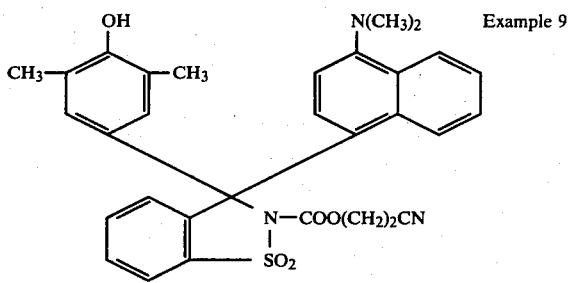

Example 9

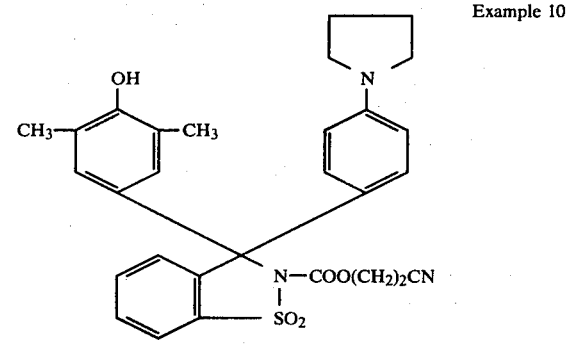

Example 10

-continued

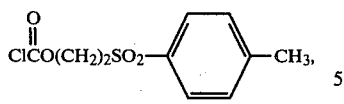

respectively.

EXAMPLE 15

Preparation of the compound having the formula:

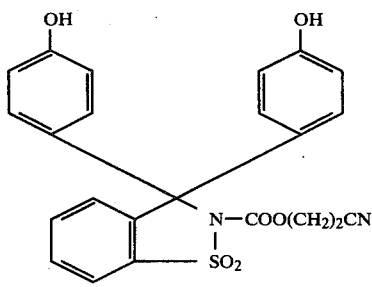

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudochloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

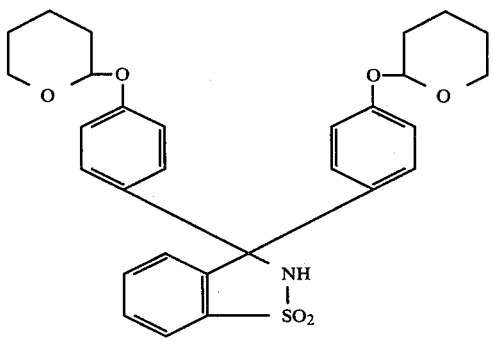

A (b) Compound A as prepared in step (a) (10.0 g.) was placed in 100 ml. of dioxane and 0.88 g. of sodium hydride (as 57% oil dispersion) was added at room temperature under nitrogen (hydrogen evolution was observed). The resultant mixture comprising the N-sodium salt of the above compound was stirred 1 hour and then 2.4 ml. of ClCOOCH$_2$CH$_2$CN was added. A white precipitate formed immediately. The reaction mixture was stirred overnight, then poured into 200 ml. water. The aqueous mixture was extracted with three 250 ml. portions of ether, which were combined and dried over sodium sulfate. The ether was removed in vacuo and the resulting solid washed with petroleum ether. Upon drying, 10.5 g. of the crude N-acylated derivative was obtained. The N-acylated compound has the formula

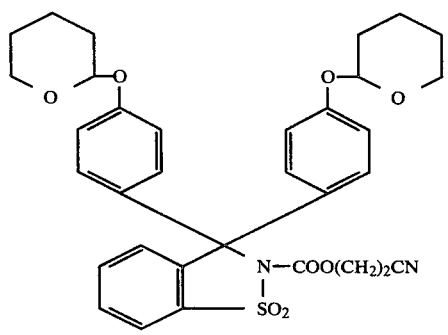

B (c) Compound B (5.0 g.) as prepared in step (b) was dissolved in 50 ml. of warm methanol which contained two drops of conc. HCl. This solution was allowed to stand at room temperature for 30 min. at which time the analysis indicated both tetrahydropyranyl protecting groups had been removed. The methanol and HCl were removed in vacuo leaving 5.0 g. of a light yellow solid which was fractionated via column chromatography (silica gel; ether) to give a pure sample of the title compound.

Tetrahydropyranylation of p-bromo-phenol used in the preparation of compound A was carried out as follows:

To 10.5 ml. of dihydropyran containing 2 drops of conc. HCl was added 10.0 g. of p-bromophenol. (The reaction was exothermic; temperature rose to 35° C.). After the addition was completed, the colorless solution obtained was heated to 50° C. and allowed to cool with stirring for 1 hour. The solution was extracted with 20 ml. of ether and 10 ml. of 10% NaOH. The ether layer was dried over anhydrous Na$_2$SO$_4$ and evaporated under reduced pressure to leave an oil. 80 ml. of ethanol was added to the oil and the resulting ethanol solution was allowed to stand. The white crystals that formed were recovered by filtration and dried under vacuum to yield 7.3 g. of the blocked phenol. The mother liquor was concentrated to one-half its original volume and cooled. More crystals formed which were isolated to yield an additional 2.1 g. of blocked phenol.

EXAMPLE 16

Preparation of the compound having the formula:

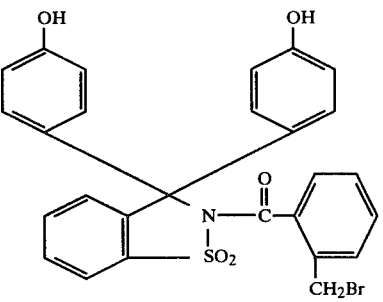

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudochloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

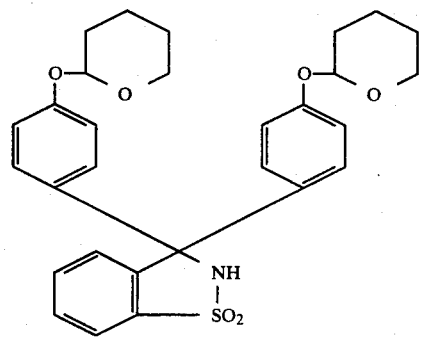

(b) 1.0 g. of the compound prepared in step (a) was placed in 15 ml. of dioxane and 0.08 g. of sodium hydride (as 57% oil dispersion) was added at room temperature under nitrogen. (Hydrogen evaluation was observed.) The resultant mixture comprising the N-sodium salt of the above compound was stirred 1 hour and then 0.342 g. of

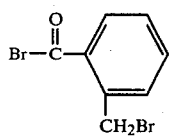

was added. A white precipitate formed immediately. The reaction mixture was stirred overnight, then poured into 100 ml. water. The white precipitate that formed was filtered, extracted with diethyl ether giving a yellow glass that was refluxed in ligroin (90°–100° C. boiling range). The ligroin was decanted leaving a solid comprising the N-acylated derivative of the above compound wherein the acyl group is

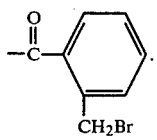

(c) To remove the 2'-tetrahydropyranyl protecting groups and obtain the product, 20 mls. of 10% HCl solution was added to the solid and the orange solid obtained was filtered and dried. A second crop of precipitate was recovered from the water precipitation which was filtered and treated with 10% HCl to give an additional 0.5 g. of solid. The solids were combined and fractionated via preparative TLC (silica gel/ether) to give a pure sample of the title compound.

EXAMPLE 17

Preparation of the compound having the formula

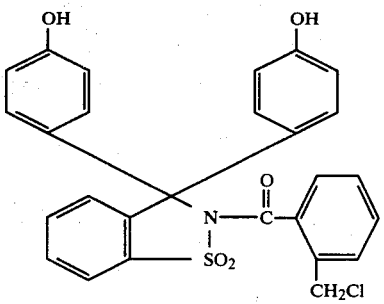

The title compound was prepared according to the procedure of Example 16 except that

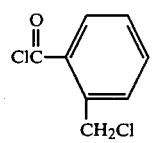

was employed as the acylating agent in step (b).

EXAMPLE 18

Preparation of the compound having the formula:

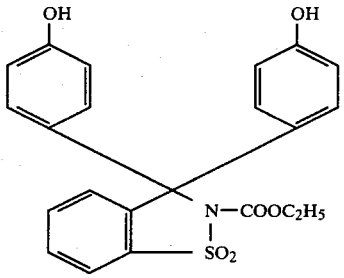

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudochloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

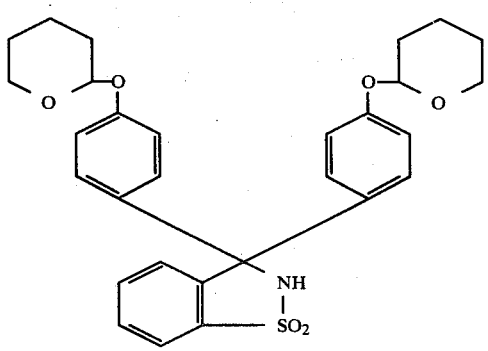

(b) The compound as prepared in step (a) (1.0 g.) was placed in 10 ml. of dioxane and 0.08 g. of sodium hydride (as 57% oil dispersion) was added at room temperature under nitrogen. (Hydrogen evolution was slow.) The solution went from light yellow to greenish then to yellow. The reaction was accelerated by heating to about 50° C. and then allowing the solution to cool to room temperature, about 1 hour. To the resulting solution comprising the N-sodium salt of Compound A was added 0.18 ml. of ethylchloroformate and the reaction mixture was stirred over the weekend.

(c) To remove the protecting groups, the solution was poured into 20 ml. of conc. HCl. After stirring for 15 minutes, the solution went from pink-red to brown. The precipitate that formed was filtered and dried under vacuum. Crystallization from 1:1 methanol-water gave 0.5 g. of the title compound as a white solid.

EXAMPLES 19 and 20

Preparation of the compounds having the formulae:

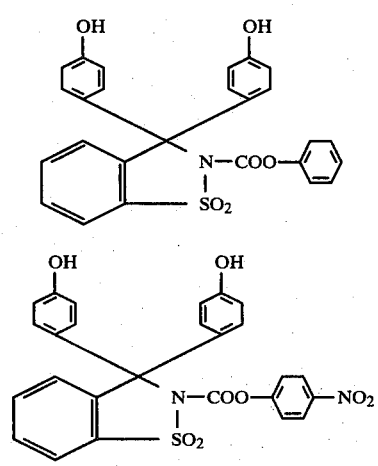

The title compounds were prepared according to the procedure described in Example 18 above except that the acylating agents employed in step (b) were

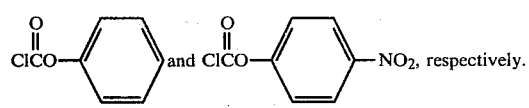

EXAMPLE 21

Preparation of the compound having the formula:

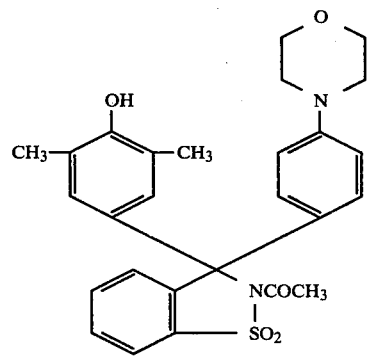

(a) N-(p-bromophenyl)morpholine (0.4 g.) was added to 20 ml. of tetrahydrofuran (THF) and the solution cooled to −65° C. To the solution was added 0.69 ml. of 2.4 M butyllithium in hexane with stirring and stirring was continued for 1 hour. (After 15 minutes the solution became cloudy and a white precipitate formed.) To this solution was added 0.5 g. of 3-(3′,5′-dimethyl-4′-methoxymethoxy-1′-phenyl)benz[d]isothiazole-1,1-dioxide in 2 ml. THF at −65° C. under nitrogen. The resulting reaction mixture was a clear orange-yellow solution. The reaction mixture was stirred for 1 hour, poured into 100 ml. of water, made acidic with conc. hydrochloric acid (pH 6), and extracted with ether. The ether was dried over $Na_2SO_4$ and evaporated leaving an oil. The oil was taken up in ligroin (boiling range 30°–60° C.) and refluxed for 1 hour. The white solid that formed was collected to give 0.7 g. of 3-(3′,5′-dimethyl-4′-methoxymethoxy-1′-phenyl)-3-(4″-N-morpholinyl-1″-phenyl)-2,3-dihydrobenz[d]isothiazole-1,1-dioxide having the formula:

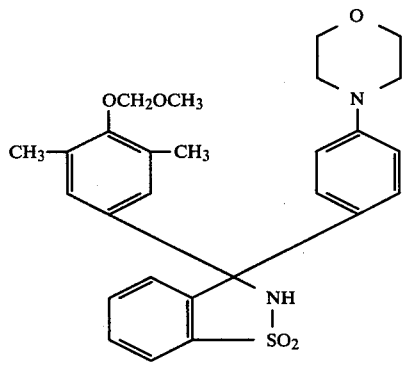

(b) The compound prepared in step (a) (0.7 g.) was dissolved in 15 ml. of pyridine under nitrogen and 0.11 ml. of

was added to the pyridine solution. A white precipitate formed. The resulting reaction solution was stirred and warmed gently (total stirring time 1 hour) and then poured into 100 ml. of water and extracted with chloroform. The chloroform was dried over anhydrous $Na_2SO_4$ and evaporated leaving a solid. The solid obtained was the N-acylated compound, 3-(3′,5′-dimethyl-4′- methoxymethoxy-1'-phenyl)-3-(4''-N-morpholinyl-1''-phenyl)-2-(acetyl)-2,3-dihydrobenz[d]isothiazole-1,1-dioxide having the formula:

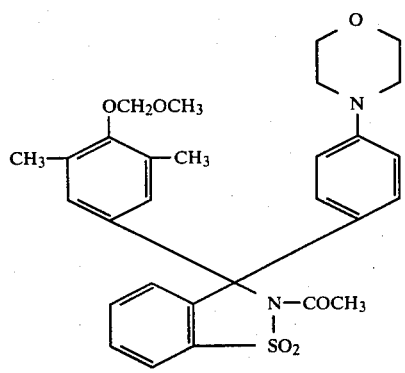

(c) The compound obtained in step (b) was then dissolved in 25 ml. of methanol, made acidic with conc. hydrochloric acid and refluxed 2 hours. The solution was evaporated leaving a tan solid. TLC of a sample on silica gel 1000 with ether gave a dark band on drying. The dark bank was removed, washed with acetone and the acetone removed after filtering to yield a gum. Ether was added to the gum and the resulting solution refluxed to give a white solid that was isolated to give the title compound.

EXAMPLES 22–24

The compounds having the formulae

Example 22

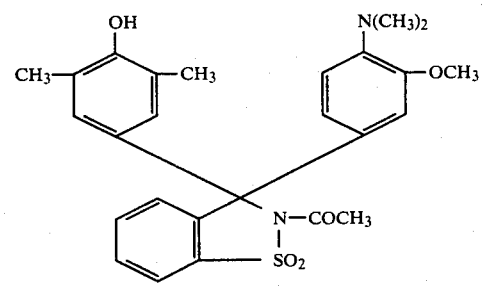

Example 23

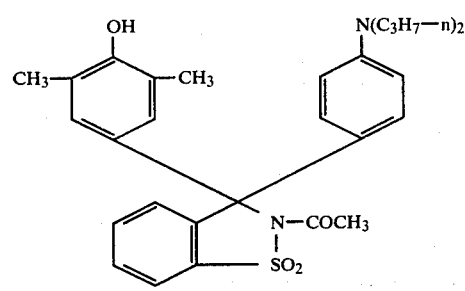

-continued

Example 24

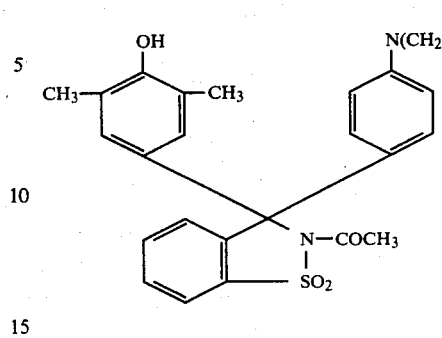

where prepared according to the procedure given in Example 21 except that in step (a) the 3-(3',5'-dimethyl-4'-methoxymethoxy-1'-phenyl)benz[d]isothiazole-1,1-dioxide was reacted with the appropriate lithium reagent, namely,

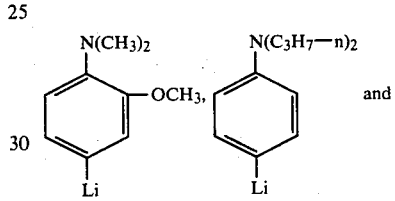 and

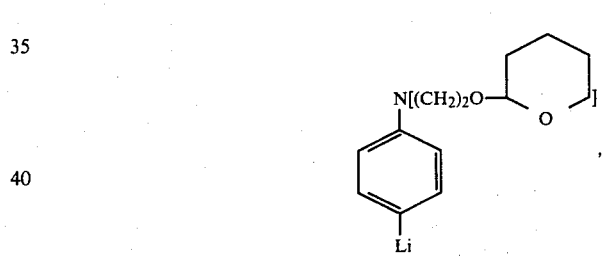

respectively, and the 2'-tetrahydropyranyl groups were removed from the -N,N-di($\beta$-hydroxyethyl)anilino moiety simultaneously with the methoxymethyl protecting group in step (c).

EXAMPLES 25 and 26

The compounds having the formulae

Example 25

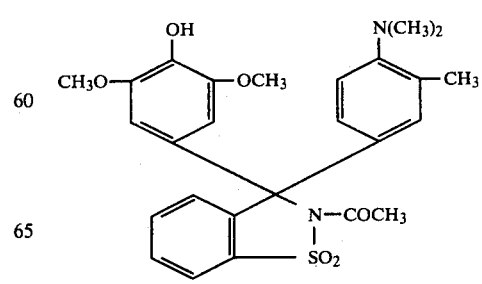

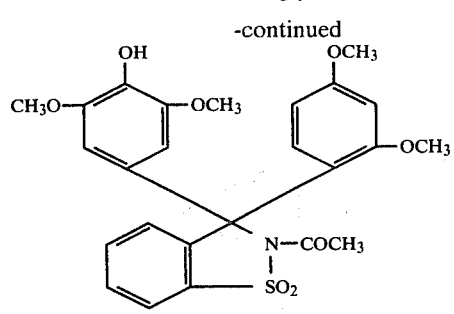

Example 26 were prepared according to the procedure given in Example 21 except that 3-(3',5'-dimethoxy-4'-methoxymethoxy-1'-phenyl)benz[d]isothiazole-1,1-dioxide was reacted with the appropriate lithium reagent, viz.,

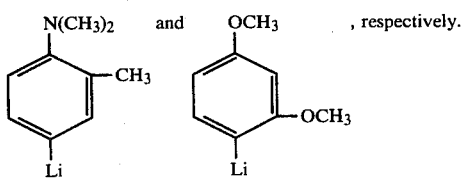

, respectively.

EXAMPLE 27

Preparation of the compound having the formula

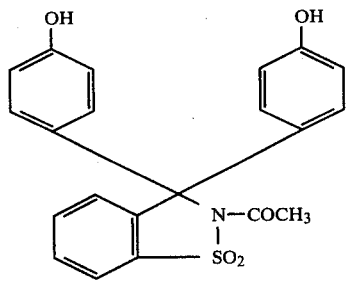

(a) 9.5 g. of p-bromoanisole in 20 ml. of dry tetrahydrofuran was added dropwise to 1.2 g. of magnesium turnings in 20 ml. of tetrahydrofuran. An $I_2$ crystal was added, and the mixture was heated to reflux. After refluxing for 1 hour, the mixture was cooled, and 5.0 g. of saccharin pseudo-chloride was added portionwise. An exotherm was observed. The reaction mixture was refluxed for 1 hour. 100 ml. of water was added followed by dilute HCl until pH 5. The mixture was then extracted with ether. The ether was dried and evaporated to leave a yellow residue. The residue was dissolved in 200 ml. of methanol and 2.0 g. of carbon black was added. The methanol solution was filtered and evaporated to leave a light yellow solid which was vacuum dried to give 8.5 g. of 3,3-di(4'-methoxy-1'-phenyl)-2,3-dihydrobenz[d]isothiazole-1,1-dioxide.

(b) 1.0 g. of the compound prepared in step (a) was dissolved in 20 ml. of dry dioxane. To this was added 0.12 g. of NaH as a 57% oil dispersion, and the solution was stirred until hydrogen evolution ceased. Additional NaH dispersion was added portionwise until no more hydrogen was evolved (about 0.05 g.). The solution was stirred for 1 hour, and 0.20 ml. of acetyl chloride was added. The temperature rose from 22° C. to 27.5° C. Stirring was continued for 3 hours at room temperature and then 200 ml. of water was slowly added. The white solid that formed was filtered, washed with water and dissolved in ether. The ether was extracted with 0.5 N NaOH, dried and evaporated to give 0.6 g. of 2-(acetyl)-3,3-di(4'-methoxy-1'-phenyl)-2,3-dihydrobenz[d]isothiazole-1,1-dioxide as a white solid.

(c) 0.5 g. of the compound prepared in step (b) was dissolved in 20 ml. of dichloromethane, cooled to −70° C. and a solution of 0.5 ml. of boron tribromide in 10 ml. of dichloromethane was added dropwise. An immediate red color formed. After addition was complete (about 10 minutes), the solution was allowed to reach room temperature, then refluxed for 3 hours and then stirred at room temperature overnight. Water was added and the dichloromethane layer was isolated, dried over sodium sulfate and evaporated to give a solid residue. The solid was extracted with ether; the ether solution was filtered and evaporated after drying to yield a pink solid (0.45 g.). The solid was dissolved in 0.5 N potassium hydroxide, extracted with ether and then the water solution was reacidified with acetic acid. The solid that formed was extracted with ether and the ether dried and evaporated to yield the title compound as an egg-white solid.

EXAMPLES 28 and 29

Preparation of the compounds having the formulae:

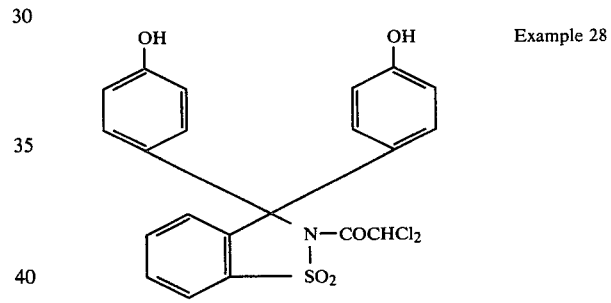

Example 28

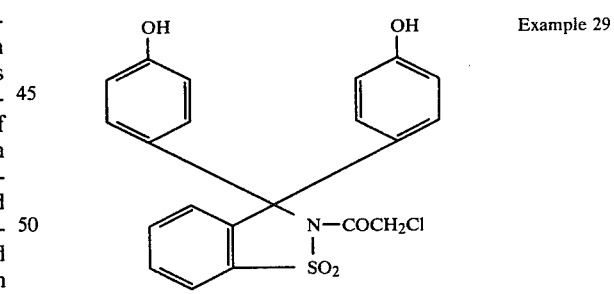

Example 29

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudo-chloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

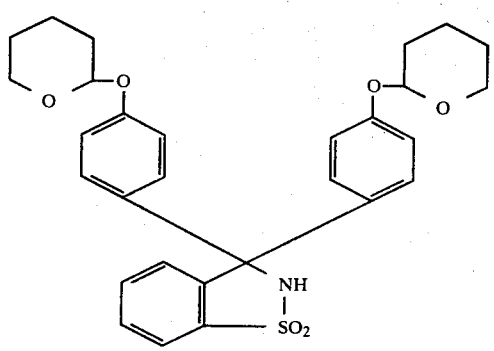

The compound prepared in step (a) was sequentially reacted with NaH and the appropriate acylating agents, namely,

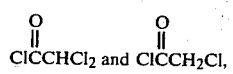

respectively, as described in step (b) of Example 27 and then the protecting groups were removed by treating the N-acylated compounds with 10% HCl solution to yield the title compounds.

EXAMPLE 30

Preparation of the compound having the formula:

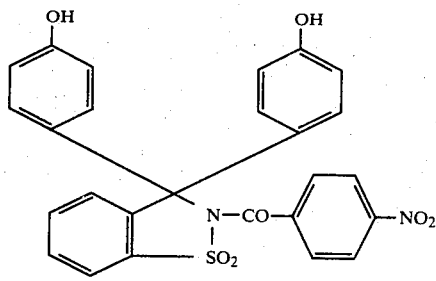

The title compound was prepared according to the procedure described in Examples 28 and 29 above except that the acylating agent employed was

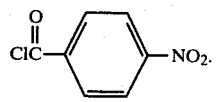

EXAMPLES 31–37

The compounds having the formulae

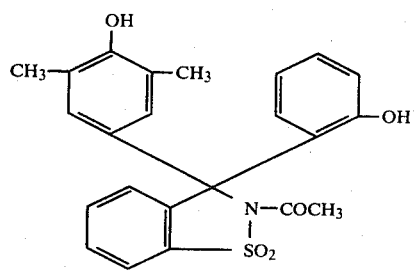
Example 31

-continued

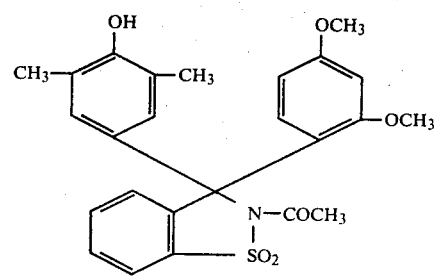
Example 32

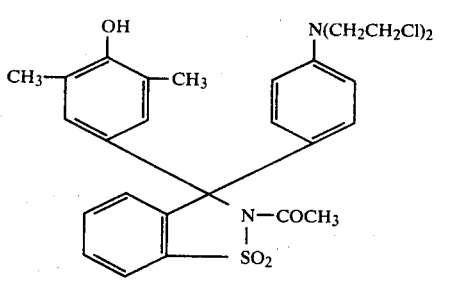
Example 33

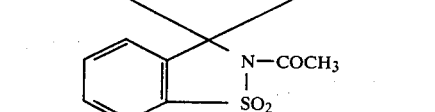

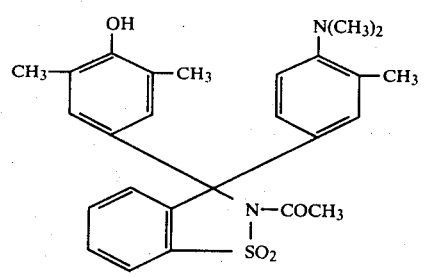
Example 34

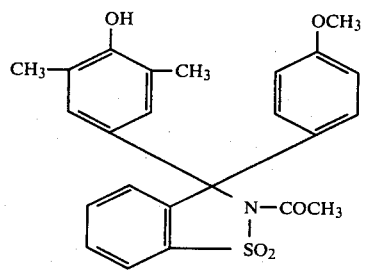
Example 35

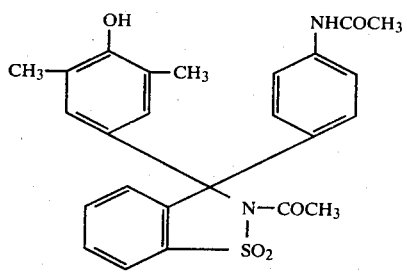
Example 36

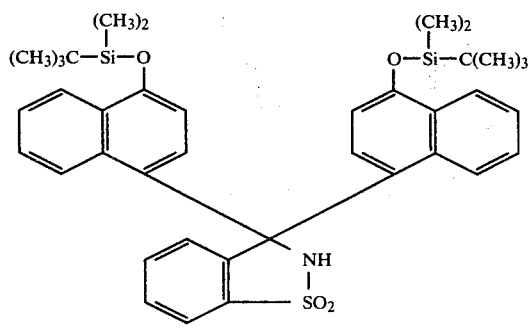

was prepared as follows:

(a) 16.87 g. of 4-bromonaphthyl dimethyl-t-butylsilyl ether was dissolved in 60 ml. of anhydrous ethyl ether under nitrogen, and the solution then cooled to −60° C. in a dry ice-acetone bath. 20.8 ml. of 2.4 N n-butyllithium in hexane was added to the cooled solution dropwise over a period of 15–20 minutes. The reaction mixture was stirred for 30 minutes and allowed to come to 15° C. over 45 minutes.

(b) The solution of step (a) was then cooled back to −40° C., and 4.63 g. of saccharin pseudo-chloride was added portionwise. After addition was complete, the reaction mixture was allowed to warm to room temperature, stirred at room temperature overnight and cooled. 50 ml. of cold water was added followed by the addition of dilute HCl until the pH reached 3–4. The ether phase was separated, and the aqueous phase was extracted with 50 ml. of ether. The ether portions were combined, washed with 100 ml. of water, dried over sodium sulfate, filtered and evaporated under reduced pressure. The residue was dissolved in iso-propanol and the iso-propanol solution slowly poured into 1 liter aqueous HCl solution having a pH of 3. The aqueous phase was decanted leaving a gummy residue. Treatment of the residue with iso-propanol and aqueous HCl (pH 3) was repeated and the final residue was dissolved in 250 ml. of iso-propanol. 3% HCl was added until precipitation ceased. The solution was allowed to stand for 10 min., the solvent decanted and water added to the gummy precipitate which on standing became crystalline. The precipitate was filtered and air-dried over the weekend to give 15.55 g. of the title compound.

The dimethyl-t-butylsilyl ether of 4-bromo-1-naphthol was prepared as follows:

4-Bromo-1-naphthol (22.1 g.) and dimethyl-t-butylsilyl chloride (18.1 g.) were dissolved in 50 ml. of dimethylformamide at room temperature. The resulting solution was cooled in an ice bath and imidazole (17.0 g.) added under nitrogen. (A slight exotherm was observed). A solid precipitated and the reaction mixture was stirred overnight.

A small sample of the crude product was treated with water adjusted to a pH of about 4–5 with dilute HCl and the solids isolated and dried. TLC on silica gel using hexane showed the product but no starting material.

The reaction mixture remaining was poured into 1500 ml. of water at about 20° C. with stirring. The pH was adjusted to 4–5 with dilute HCl, and the solids were filtered, washed with water, and air-dried for 2 hours and dissolved in 150 ml. of boiling isopropanol. The isopropanol solution was filtered while hot and then cooled slowly to room temperature. Crystals began to form and after standing at room temperature overnight, the solution was cooled in an ice water bath for 1 hour and filtered. The solid collected was washed with small amounts of isopropanol, air-dried briefly and then dried in vacuo for 2 hours to give 24.3 g. of the title compound (melting range 70°–73° C.).

The 3,3-di[4'-(2''-tetrahydropyranyloxy)-1'-phenyl]-2,3-dihydrobenz[d]isothiazole-1,1-dioxide having the formula

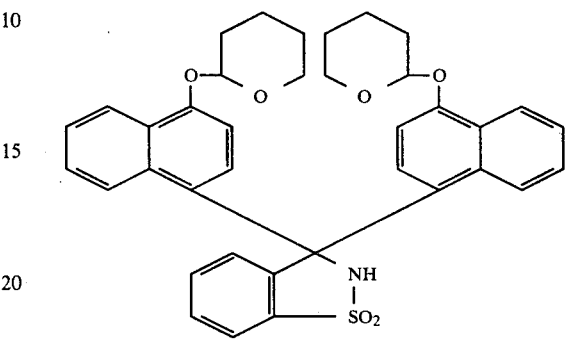

was prepared in the same manner as the phenol analog.

The methoxymethyl ether and 2'-tetrahydropyranyl ether of 4-bromo-1-naphthol were prepared according to the procedures described above and the methoxymethyl and 2'-tetrahydropyranyl ethers of 4-bromo-1-naphthol were converted to the corresponding 4-lithium derivatives by reaction with n-butyllithium according to the procedures described above.

It will be appreciated that the lithium derivatives of the blocked 1-naphthols may be reacted with the N-lithium salt of saccharin to give the corresponding 3-(4'-OP-1'-naphthyl)-benz[d]isothiazole-1,1-dioxide which, in turn, may be reacted with the selected phenyllithium or naphthyllithium reagent to give the corresponding 3-(4'-OP-1'-naphthyl)-3-(phenyl/naphthyl)-2,3-dihydrobenz[d]isothiazole-1,1-dioxide.

Where it is desired to prepare sulfamnaphthaleins, 2,3-dihydro-3-oxo-naphtho[1,8-de]1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with PCl5 as described above for the preparation of saccharin pseudo-chloride.

As mentioned above, the compounds of the present invention are useful as intermediates in the synthesis of certain 3,5-disubstituted-2,3-dihydrobenz[d]isothiazole-1,1-dioxides possessing a carbonyl group in the 2-position. Such compounds possessing a 4'-hydroxyphenyl moiety as one of the 3,3 substituents and a phenyl/-naphthyl or 4'-substituted phenyl/4'-substituted naphthyl moiety as the other of the 3,3 substituents form the subject matter of copending U.S. patent application Ser. No. 836,021 now U.S. Pat. No. 4,204,061 of Stanley M. Bloom, Alan L. Borror and James W. Foley filed concurrently herewith and of copending U.S. patent applications Ser. Nos. 835,998 now U.S. Pat. No. 4,178,446, 836,005 now U.S. Pat. No. 4,231,929 and 836,009 now U.S. Pat. No. 4,228,075 of Alan L. Borror and James W. Foley also filed concurrently herewith. As discussed in the aforementioned applications, compounds may be selected for use as classical pH-sensitive indicator dyes or as photographic optical filter agents and filter agent

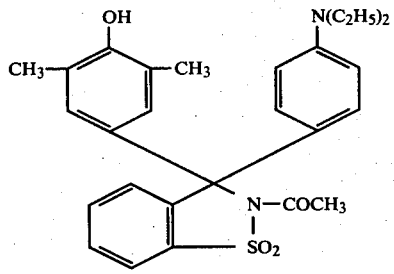

Example 37 were prepared by reacting 3-(3',5'-dimethyl-4'-methoxymethoxy-1'-phenyl)benz[d]isothiazole-1,1-dioxide with the selected aryl lithium reagent as described in step (a) of Example 21 above to give the corresponding 3,3-disubstituted-2,3-dihydrobenz[d]isothiazole-1,1-dioxide. The lithium reagents employed were

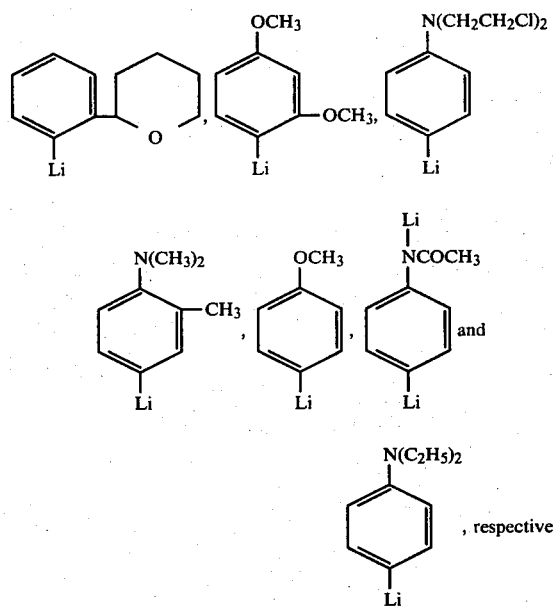

, respectively.

The 3,3-disubstituted-2,3-dihydrobenz[d]isothiazole-1,1-dioxides obtained were then sequentially reacted with NaH and

as described in Example 27 to give the corresponding

intermediates. The intermediates were then treated with dilute hydrochloric acid to remove the protecting group(s) to give the title compounds.

EXAMPLE 38

The compound having the formula

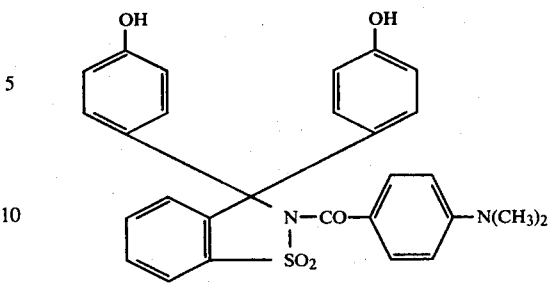

was prepared according to the procedure described in Examples 28 and 29 except that the acylating agent employed was

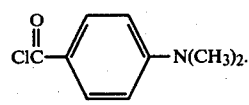

EXAMPLE 39

Preparation of the compound having the formula:

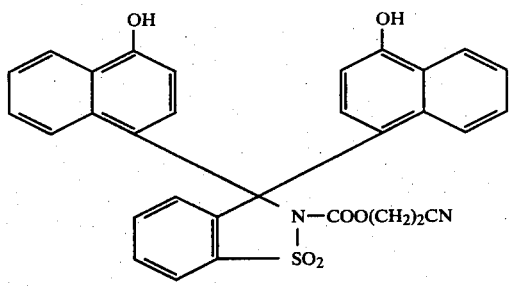

(a) To a solution of 168 mg. of t-potassium butoxide in 5 ml. of dry tetrahydrofuran was added 834 mg. of 3,3-di[4'-(2''-tetrahydropyranyloxy)-1'-naphthyl]-2,3-dihydrobenz[d]isothiazole-1,1-dioxide in several small portions under nitrogen. The yellow-brown solution obtained was stirred for 2 hours at room temperature and then cooled in an ice bath.

(b) To the cooled solution of step (a) was added dropwise 267 mg. of β-cyanoethylchloroformate. (The color changed to light yellow). The resulting solution was stirred over the weekend at room temperature under nitrogen during which time most of the solvent had evaporated leaving yellow-orange solids comprising the title compound and deblocked starting material.

(c) The yellow-orange solids were taken up in 25 ml. of ether and the ether solution concentrated to about 10 ml. The crystals that formed were filtered, washed with ether and the orange and yellow components separated by preparative TLC on (silica gel/ether). The orange component was removed by eluting with n-butanol and the yellow component was removed by eluting with methanol. The methanol was then evaporated to give the title compound.

The intermediate having the formula precursors depending upon the 2-substituent of the benz[d]isothiazole ring. The photographic use of certain of the compounds as photographic optical filter agents and filter agent precursors forms the subject matter of copending U.S. patent application Ser. No. 836,006, now U.S. Pat. No. 4,138,381 of Stanley M. Bloom, Alan L. Borror and James W. Foley filed concurrently herewith. The 2,3-dihydrobenz[d]isothiazole-1,1-dioxides possessing a 4'-hydroxynaphthyl moiety as one of the 3,3 substituents and a naphthyl or 4'-substituted naphthyl moiety as the other of the 3,3 substituents form the subject matter of copending U.S. patent application Ser. No. 836,067 now U.S. Pat. No. 4,195,180 of Alan L. Borror, Louis Cincotta, Ernest W. Ellis and James W. Foley filed concurrently herewith, and as described therein, compounds may be selected for use as classical pH-sensitive indicator dyes or as antihalo dyes in photography.

Since certain changes may be made in the above processes and products without departing from the scope of the invention herein involved, it is intended that all matter contained in the above description shall be interpreted as illustrative and not in a limiting sense.

What is claimed is:

1. A compound of the formula

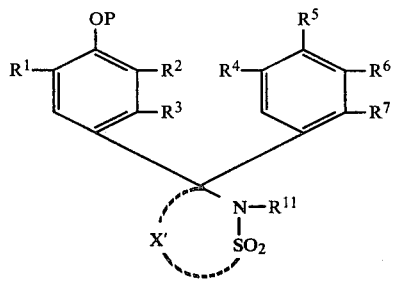

wherein P is a protecting group, $R^1$ and $R^2$ each are selected from hydrogen, alkyl, alkoxy, chloro and fluoro; $R^3$ is hydrogen, alkyl, alkoxy, or —OP; $R^2$ and $R^3$ taken together represent the carbon atoms necessary to complete a fused benzene ring; $R^4$ and $R^6$ each are selected from hydrogen, alkyl, alkoxy, chloro and fluoro; $R^5$ is hydrogen, alkyl, alkoxy, —OP$^I$ wherein P$^I$ is a protecting group, —N,N-(dialkyl)amino, —N,N-(w-R$^8$alkyl)$_2$amino wherein $R^8$ is halo or —OP$^{II}$ wherein P$^{II}$ is a protecting group, —NHCOCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —OP$^{III}$ wherein P$^{III}$ is a protecting group the same as P$^I$ or P$^{II}$; $R^6$ and $R^7$ taken together represent the carbon atoms necessary to complete a fused benzene ring; $R^4$, $R^5$ and $R^6$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and $R^{11}$ is

wherein $R^9$ is selected from methyl, methyl substituted with at least one halo group selected from chloro, bromo and fluoro, alkoxy having 1 to 4 carbon atoms, phenyl, phenyl substituted in the para position with alkyl having 1 to 4 carbon atoms or —N,N-(dialkyl)amino, phenyl substituted with at least one electron-withdrawing group, phenoxy, phenoxy substituted with at least one electron-withdrawing group, —O(CH$_2$)$_2$Y wherein Y is an electron-withdrawing group and phenyl substituted in the ortho position with —CH$_2$R$^{10}$ wherein $R^{10}$ is chloro or bromo.

2. A compound as defined in claim 50 wherein X represents the atoms necessary to complete 2,3-dihydrobenz[d]isothiazole-1,1-dioxide.

3. A compound as defined in claim 1 wherein $R^9$ is methyl.

4. A compound as defined in claim 1 wherein $R^9$ is methyl substituted with at least one halo group selected from chloro, bromo and fluoro.

5. A compound as defined in claim 1 wherein $R^9$ is alkoxy having 1 to 4 carbon atoms.

6. A compound as defined in claim 1 wherein $R^9$ is phenyl.

7. A compound as defined in claim 1 wherein $R^9$ is phenyl substituted in the para position with alkyl having 1 to 4 carbon atoms or —N,N-(dialkyl)amino.

8. A compound as defined in claim 1 wherein $R^9$ is phenyl substituted with at least one electron-withdrawing group.

9. A compound as defined in claim 1 wherein $R^9$ is phenoxy.

10. A compound as defined in claim 1 wherein $R^9$ is phenoxy substituted with at least one electron-withdrawing group.

11. A compound as defined in claim 1 wherein $R^9$ is —O(CH$_2$)$_2$Y wherein Y is an electron-withdrawing group.

12. A compound as defined in claim 1 wherein $R^9$ is —CH$_2$R$^{10}$ wherein $R^{10}$ is chloro or bromo.

13. A compound as defined in claim 1 wherein said $R^1$ and $R^2$ each are alkyl.

14. A compound as defined in claim 13 wherein said $R^3$ is hydrogen.

15. A compound as defined in claim 1 wherein said $R^1$ and $R^2$ each are alkoxy.

16. A compound as defined in claim 15 wherein said $R^3$ is hydrogen.

17. A compound as defined in claim 14 wherein said $R^5$ is —OP$^I$.

18. A compound as defined in claim 17 wherein said $R^4$ and $R^6$ are alkyl and said $R^7$ is hydrogen.

19. A compound as defined in claim 16 wherein said $R^5$ is —OP$^I$.

20. A compound as defined in claim 19 wherein said $R^4$ and $R^6$ are alkoxy and said $R^7$ is hydrogen.

21. A compound as defined in claim 18 wherein said $R^1$, $R^2$, $R^4$ and $R^6$ each are methyl.

22. A compound as defined in claim 20 wherein said $R^1$, $R^2$, $R^4$ and $R^6$ each are methoxy.

23. A compound as defined in claim 14 wherein said $R^1$ and $R^2$ are methyl and $R^4$, $R^6$ and $R^7$ are hydrogen.

24. A compound as defined in claim 23 wherein said $R^5$ is morpholino.

25. A compound as defined in claim 23 wherein said $R^5$ is —N,N-(dialkyl)amino.

26. A compound as defined in claim 23 wherein said $R^5$ is —N,N-(w-R$^8$alkyl)$_2$amino.

27. A compound as defined in claim 23 wherein said $R^5$ is alkoxy.

28. A compound as defined in claim 23 wherein said $R^5$ is —NHCOCH$_3$.

29. A compound as defined in claim 23 wherein said $R^5$ is pyrrolidino.

30. A compound as defined in claim 23 wherein said $R^5$ is tetrahydro-2H,4H-1,3,6-dioxazocino.

31. A compound as defined in claim 14 wherein said $R^1$ and $R^2$ are methyl, $R^4$ is hydrogen, $R^5$ is —N,N-(dialkyl)amino and $R^6$ and $R^7$ represent the carbon atoms necessary to complete a fused benzene ring.

32. A compound as defined in claim 14 wherein said $R^1$ and $R^2$ are methyl, $R^4$ and $R^6$ are hydrogen, $R^5$ is —N,N-(dialkyl)amino and $R^7$ is alkyl.

33. A compound as defined in claim 14 wherein said $R^1$ and $R^2$ are methyl, $R^4$, $R^5$ and $R^6$ are hydrogen and $R^7$ is —$OP^{III}$.

34. A compound as defined in claim 16 wherein said $R^1$ and $R^2$ are methoxy, $R^4$ and $R^6$ are hydrogen and $R^5$ and $R^7$ are alkoxy.

35. A compound as defined in claim 1 wherein said $R^1$, $R^2$, $R^3$, $R^4$, $R^5$, $R^6$ and $R^7$ are hydrogen.

36. A compound as defined in claim 1 wherein P, $P^I$, $P^{II}$, and $P^{III}$ are 2'-tetrahydropyranyl, methoxymethyl or dimethyl-t-butylsilyl.

37. The compound

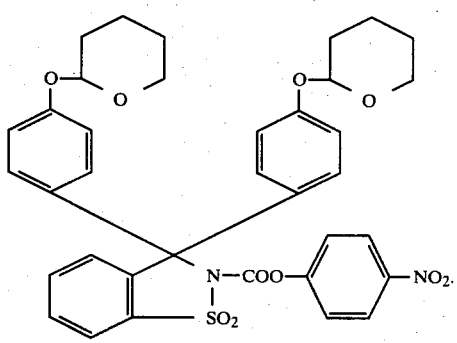

38. The compound

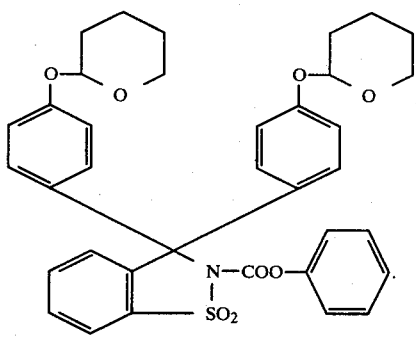

39. The compound

40. The compound

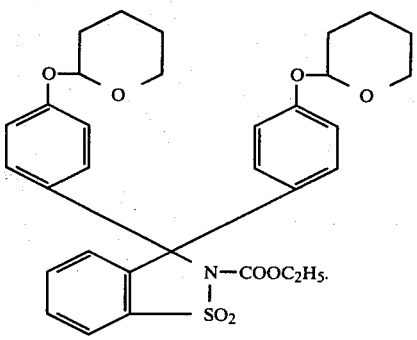

41. The compound

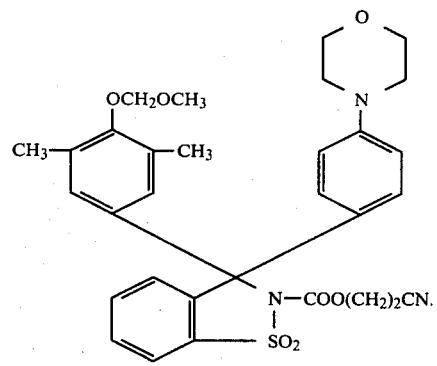

42. The compound

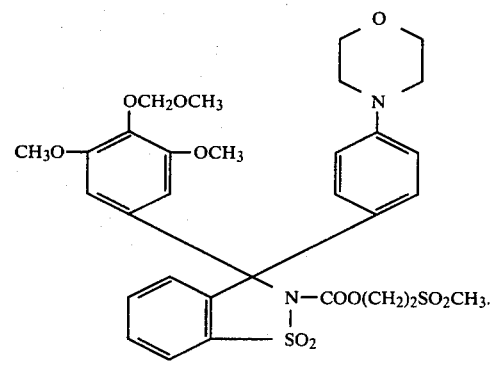

43. The compound

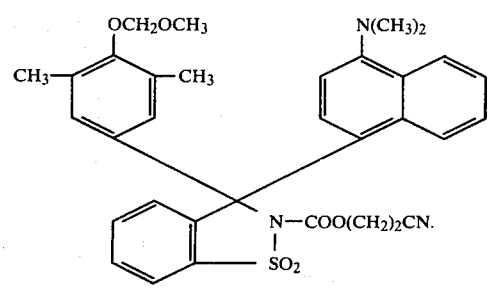

44. The compound
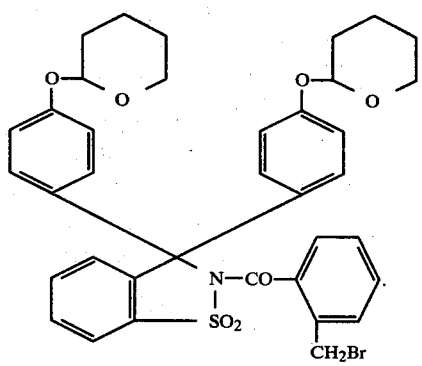
45. The compound
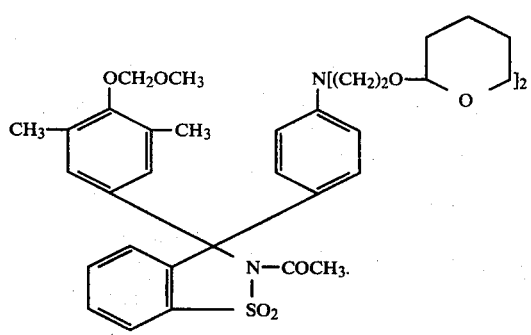
46. The compound
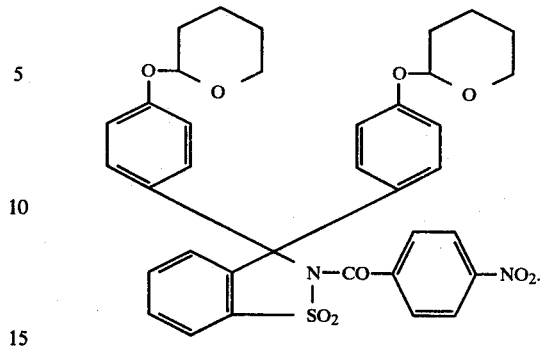
47. The compound
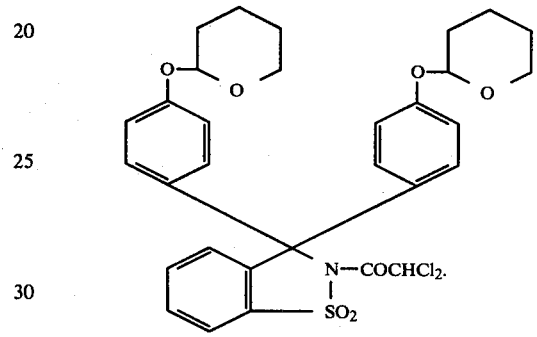
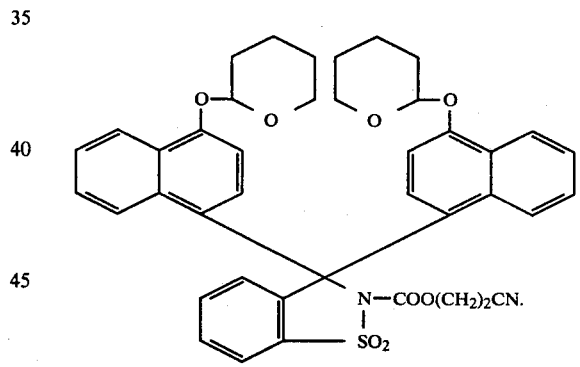
* * * * *